(12) United States Patent
Kostrzewski

(10) Patent No.: US 10,722,231 B2
(45) Date of Patent: *Jul. 28, 2020

(54) SURGICAL INSTRUMENT

(71) Applicant: Covidien LP, Mansfield, MA (US)

(72) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 227 days.

This patent is subject to a terminal disclaimer.

(21) Appl. No.: 15/867,897

(22) Filed: Jan. 11, 2018

(65) Prior Publication Data
US 2018/0132847 A1    May 17, 2018

Related U.S. Application Data

(63) Continuation of application No. 14/507,877, filed on Oct. 7, 2014, now Pat. No. 9,901,341.

(Continued)

(51) Int. Cl.
*A61B 17/072*    (2006.01)
*A61B 17/068*    (2006.01)
(Continued)

(52) U.S. Cl.
CPC .......... *A61B 17/072* (2013.01); *A61B 17/068* (2013.01); *A61B 17/105* (2013.01);
(Continued)

(58) Field of Classification Search
CPC . A61B 17/072; A61B 17/3211; A61B 17/105; A61B 17/068; A61B 2017/2927;
(Continued)

(56) References Cited

U.S. PATENT DOCUMENTS 1,385,970 A  *  7/1921  Norton ................... B24B 47/04
                                                        74/425
3,418,881 A  *  12/1968  Yasuhara ............... B23F 23/08
                                                        409/3

(Continued)

FOREIGN PATENT DOCUMENTS

EP    0634144 A1    1/1995
EP    2586382 A2    5/2013

OTHER PUBLICATIONS

Extended European Search Report issued in corresponding European Appln. No. EP 15167798 dated Feb. 2, 2016.

*Primary Examiner* — Robert F Long
(74) *Attorney, Agent, or Firm* — Carter, DeLuca & Farrell LLP

(57) ABSTRACT

A surgical stapling apparatus for progressively stapling and forming an incision in body tissue is provided. The apparatus includes a body portion and a tool assembly supported on the body portion. The apparatus further includes an input cam member slidable within the body portion, a drum member rotatably supported within the body portion, and an output cam member slidable within the body portion. The drum member is coupled to the input cam member such that linear movement of the input cam member effects rotatable movement of the drum member. The output cam member is coupled to the drum member such that rotatable movement of the drum member effects linear movement of the output cam member. Linear movement of the input cam member effects movement of an anvil in relation to a cartridge between unclamped and clamped positions.

18 Claims, 31 Drawing Sheets

Related U.S. Application Data

(60) Provisional application No. 61/994,155, filed on May 16, 2014.

(51) Int. Cl.
  *A61B 17/10* (2006.01)
  *A61B 17/3211* (2006.01)
  *A61B 17/00* (2006.01)
  *A61B 17/29* (2006.01)

(52) U.S. Cl.
  CPC . *A61B 17/3211* (2013.01); *A61B 2017/00473* (2013.01); *A61B 2017/07221* (2013.01); *A61B 2017/07228* (2013.01); *A61B 2017/07257* (2013.01); *A61B 2017/07271* (2013.01); *A61B 2017/07285* (2013.01); *A61B 2017/2916* (2013.01); *A61B 2017/2927* (2013.01); *A61B 2017/32113* (2013.01)

(58) Field of Classification Search
  CPC .. A61B 2017/2916; A61B 2017/07285; A61B 2017/07271; A61B 2017/07257; A61B 2017/07228; A61B 2017/07221; A61B 2017/00473; A61B 2017/32113; A61B 17/115
  USPC .............................. 227/175.1–182.1
  See application file for complete search history.

(56) References Cited

U.S. PATENT DOCUMENTS

| | | | |
|---|---|---|---|
| 3,499,591 A | 3/1970 | Green | |
| 3,583,245 A * | 6/1971 | Schaefer | F15B 15/063 74/57 |
| 3,692,224 A | 9/1972 | Kstafiev et al. | |
| 4,442,964 A | 4/1984 | Becht | |
| 4,522,327 A | 6/1985 | Korthoff et al. | |
| 4,527,724 A | 7/1985 | Chow et al. | |
| 4,591,085 A | 5/1986 | Di Giovanni | |
| 4,728,020 A | 3/1988 | Green et al. | |
| 4,771,807 A * | 9/1988 | Karani | F16K 31/05 137/553 |
| 5,240,163 A | 8/1993 | Stein et al. | |
| 5,269,064 A * | 12/1993 | Greene | B27G 19/003 30/371 |
| 5,307,976 A | 5/1994 | Olson et al. | |
| 5,312,023 A * | 5/1994 | Green | A61B 17/07207 227/175.1 |
| 5,318,221 A | 6/1994 | Green et al. | |
| 5,326,013 A | 7/1994 | Green et al. | |
| 5,456,401 A | 10/1995 | Green et al. | |
| 5,478,003 A | 12/1995 | Green et al. | |
| 5,485,952 A | 1/1996 | Fontayne | |
| 5,501,846 A * | 3/1996 | Pavelle | H01M 8/04223 422/211 |
| 5,533,581 A * | 7/1996 | Barth | B23Q 5/045 173/216 |
| 5,560,532 A | 10/1996 | DeFonzo et al. | |
| 5,636,780 A | 6/1997 | Green et al. | |
| 5,645,209 A | 7/1997 | Green et al. | |
| 5,690,269 A | 11/1997 | Bolanos et al. | |
| 5,715,490 A * | 2/1998 | Ishito | G03B 13/12 396/378 |
| 5,797,959 A | 8/1998 | Castro et al. | |
| 5,901,895 A | 5/1999 | Heaton et al. | |
| 5,993,464 A | 11/1999 | Knodel | |
| 6,250,532 B1 | 6/2001 | Green et al. | |
| 6,460,749 B1 | 10/2002 | Levinson et al. | |
| 6,619,529 B2 | 9/2003 | Green et al. | |
| 7,513,407 B1 * | 4/2009 | Chang | B25C 1/06 173/202 |
| 7,516,877 B2 | 4/2009 | Aranyi | |
| 7,600,663 B2 | 10/2009 | Green | |
| 7,914,543 B2 * | 3/2011 | Roth | A61B 17/07207 227/175.1 |
| 8,029,035 B1 * | 10/2011 | Bottner | B25J 1/04 294/104 |
| 9,649,110 B2 | 5/2017 | Parihar et al. | |
| 9,901,341 B2 | 2/2018 | Kostrzewski | |
| 2002/0063143 A1 | 5/2002 | Adams et al. | |
| 2003/0105478 A1 * | 6/2003 | Whitman | A61B 17/07207 606/167 |
| 2005/0006432 A1 * | 1/2005 | Racenet | A61B 17/07207 227/176.1 |
| 2008/0083809 A1 | 4/2008 | Scirica | |
| 2008/0110958 A1 * | 5/2008 | McKenna | A61B 17/00491 227/176.1 |
| 2009/0229391 A1 * | 9/2009 | Eakin | F16H 27/04 74/117 |
| 2009/0283568 A1 | 11/2009 | Racenet et al. | |
| 2010/0193567 A1 | 8/2010 | Scheib et al. | |
| 2010/0320252 A1 | 12/2010 | Viola et al. | |
| 2011/0248064 A1 | 10/2011 | Marczyk | |
| 2012/0078244 A1 * | 3/2012 | Worrell | A61B 17/07207 606/33 |
| 2012/0199632 A1 * | 8/2012 | Spivey | A61B 34/71 227/176.1 |
| 2012/0205421 A1 * | 8/2012 | Shelton, IV | A61B 17/072 227/177.1 |
| 2013/0062090 A1 * | 3/2013 | Winnard | B25B 17/02 173/216 |
| 2013/0112730 A1 * | 5/2013 | Whitman | A61B 17/07207 227/175.1 |
| 2013/0214030 A1 * | 8/2013 | Aronhalt | A61B 17/1155 227/176.1 |
| 2015/0272569 A1 | 10/2015 | Leimbach et al. | |
| 2015/0320423 A1 * | 11/2015 | Aranyi | A61B 17/105 227/177.1 |
| 2015/0368959 A1 * | 12/2015 | Holford | E06B 7/10 49/82.1 |
| 2016/0183938 A1 * | 6/2016 | Whitman | A61B 17/07207 227/175.1 |
| 2016/0367248 A1 * | 12/2016 | Baxter, III | A61B 17/068 |
| 2016/0367255 A1 | 12/2016 | Wise et al. | |
| 2018/0168580 A1 * | 6/2018 | Hunter | A61B 90/94 |
| 2019/0183484 A1 * | 6/2019 | Malkowski | A61B 17/0469 |

\* cited by examiner

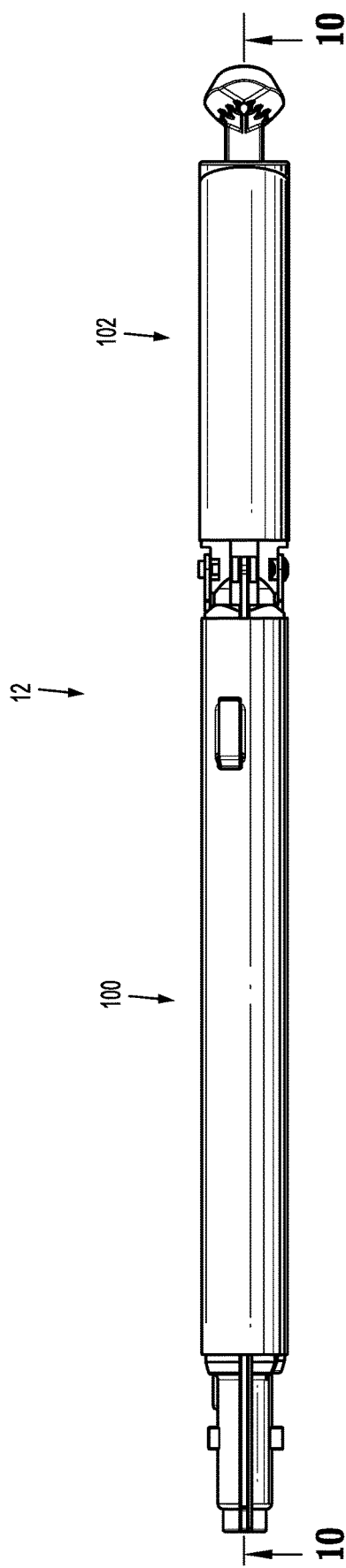
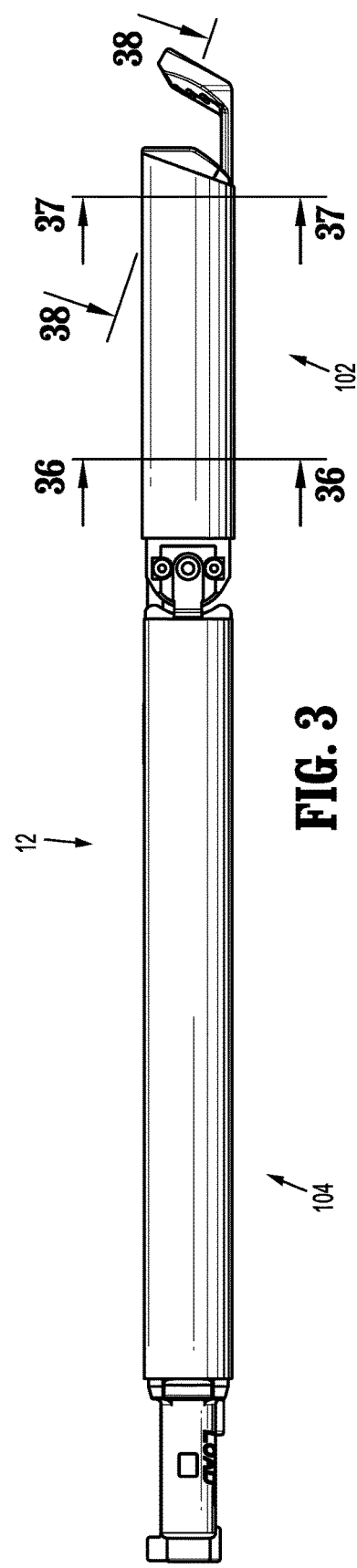
FIG. 2
FIG. 3

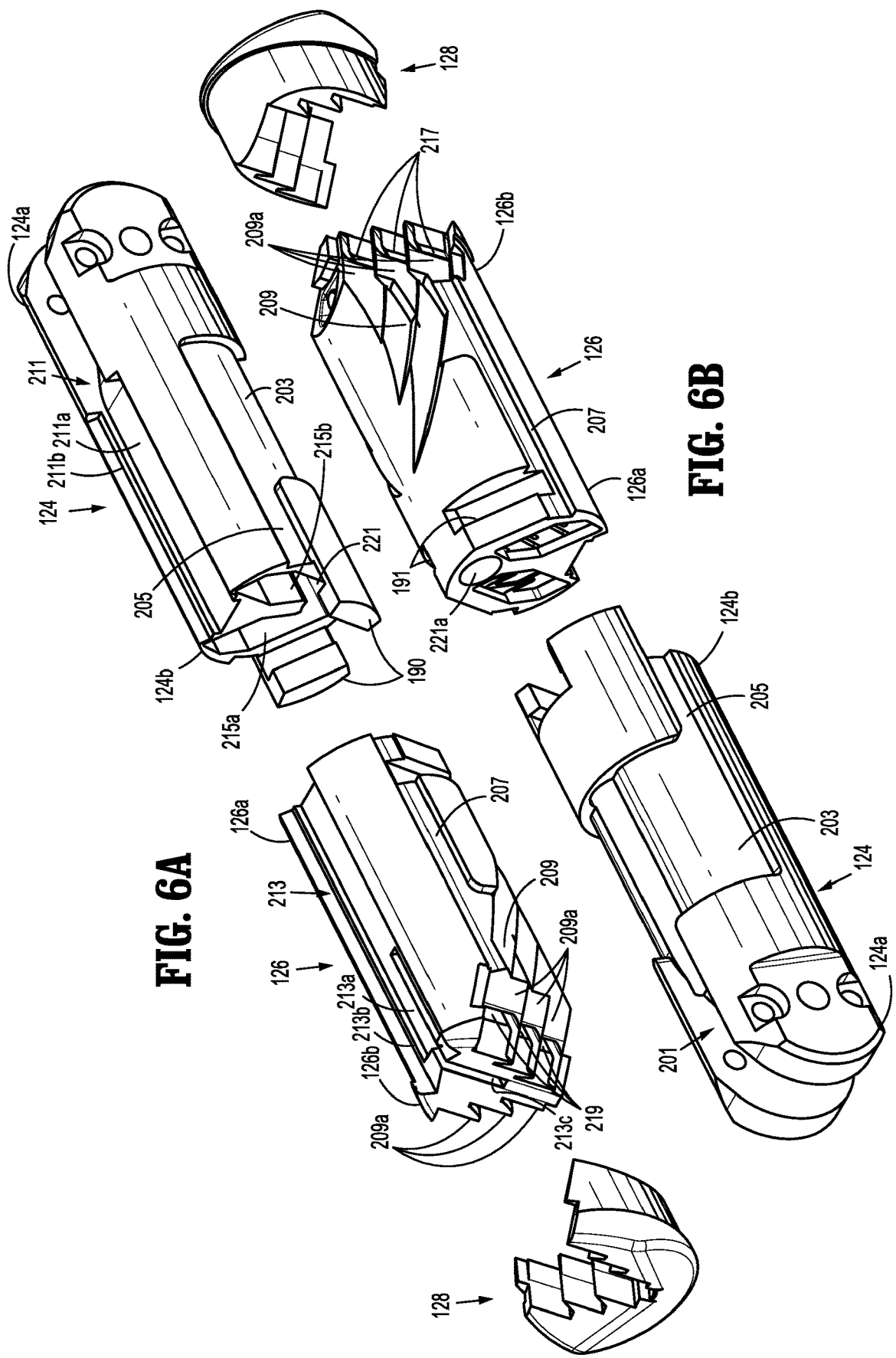

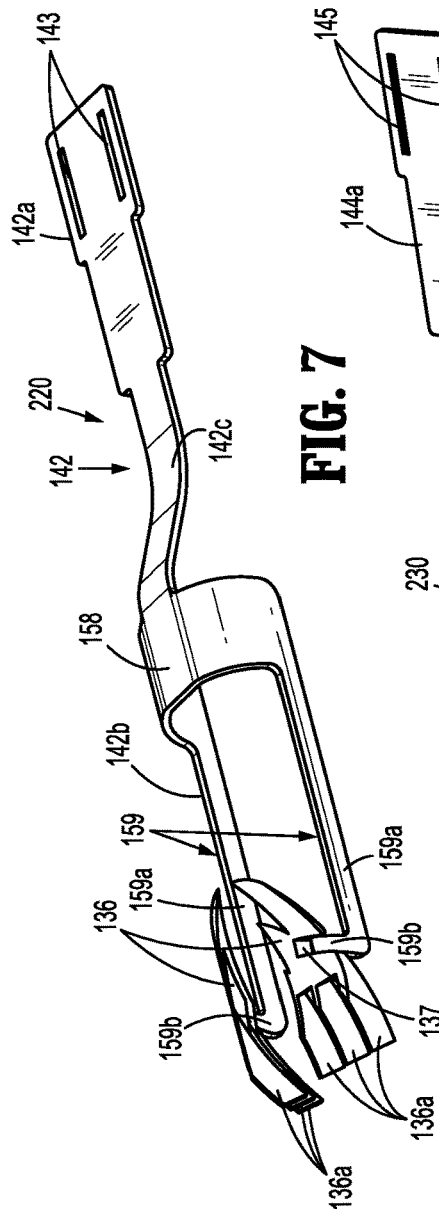
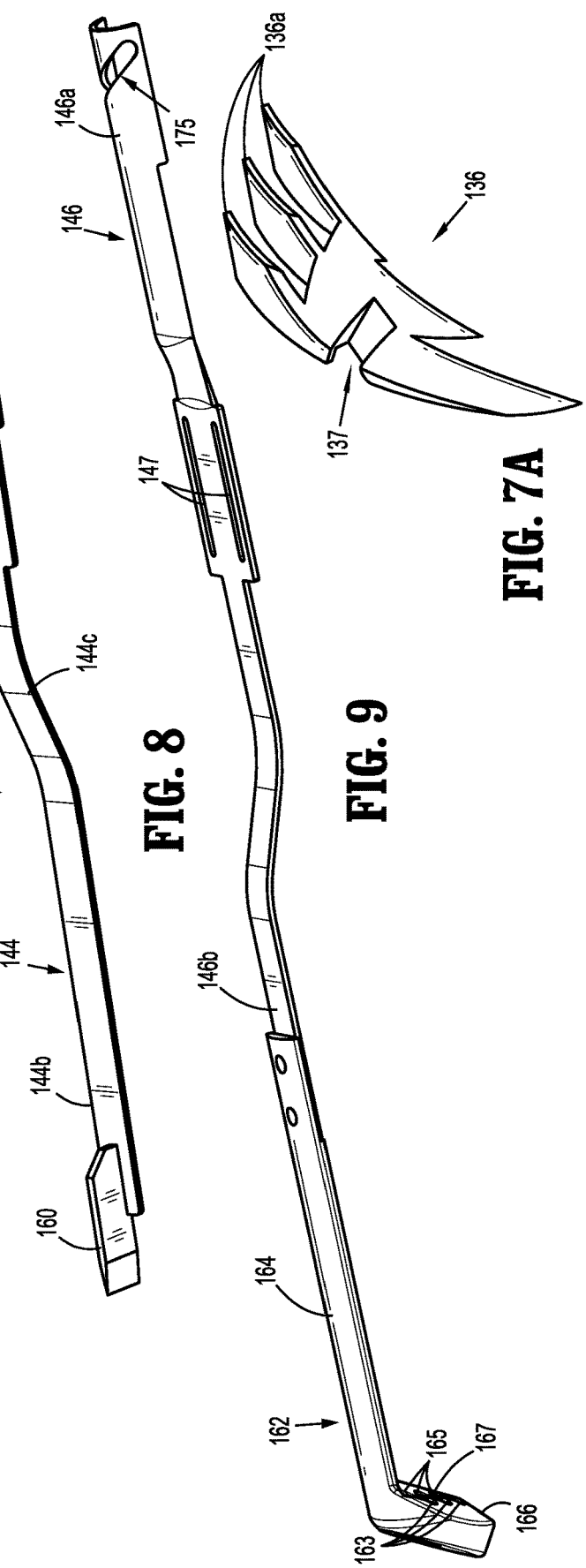
FIG. 7
FIG. 7A
FIG. 8
FIG. 9

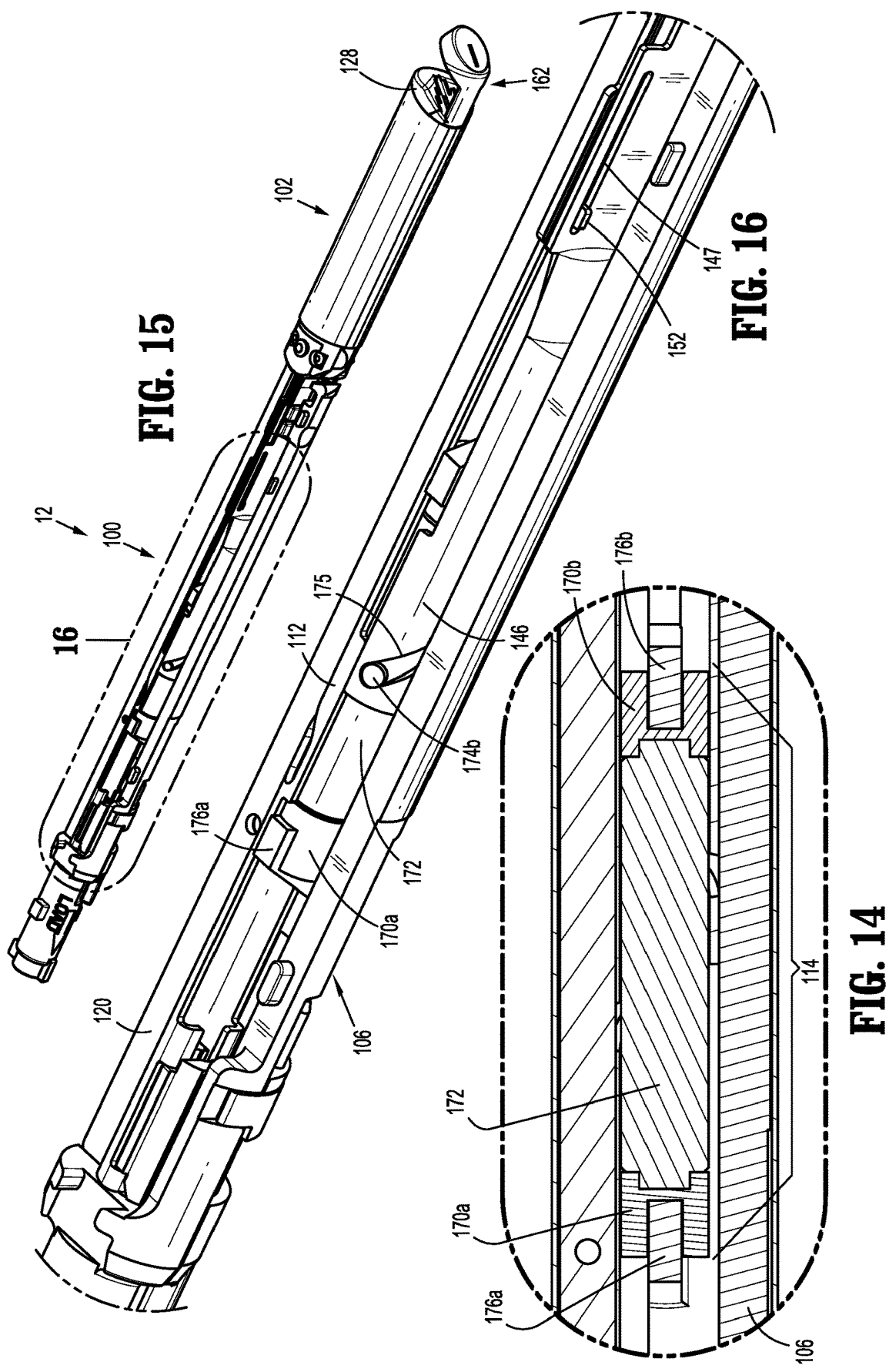

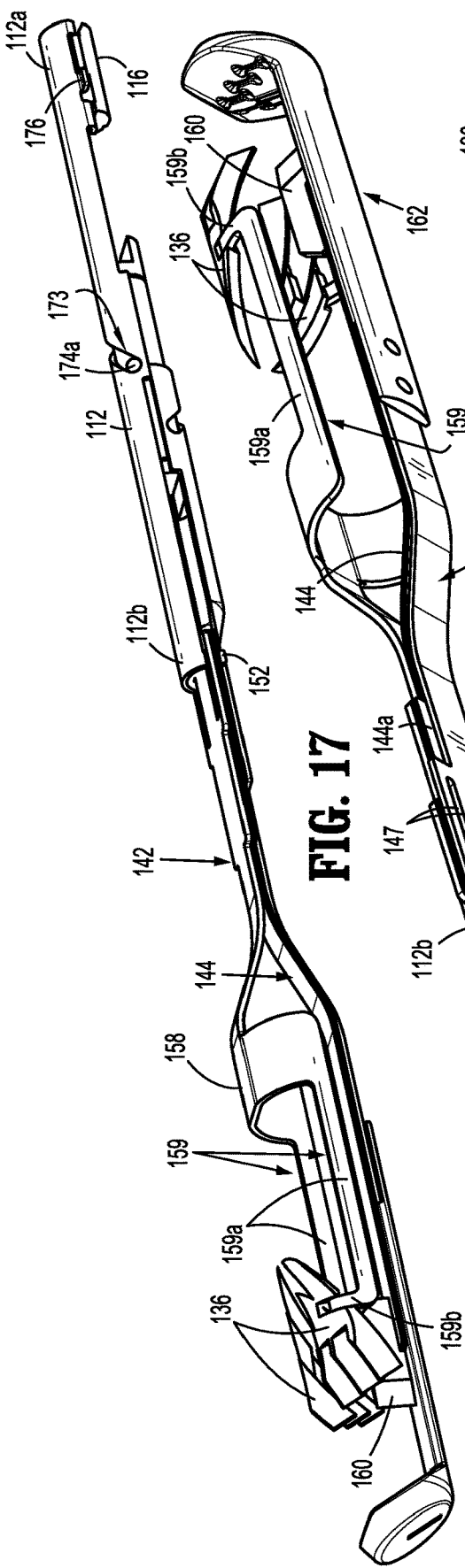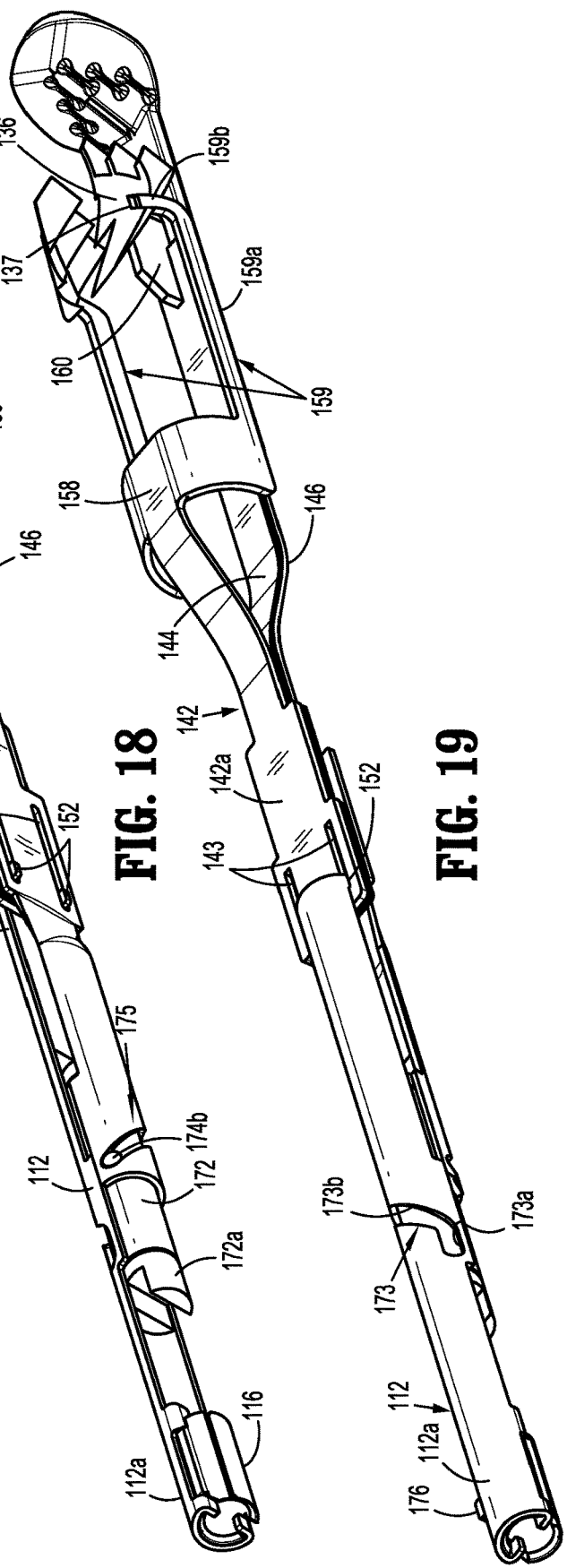

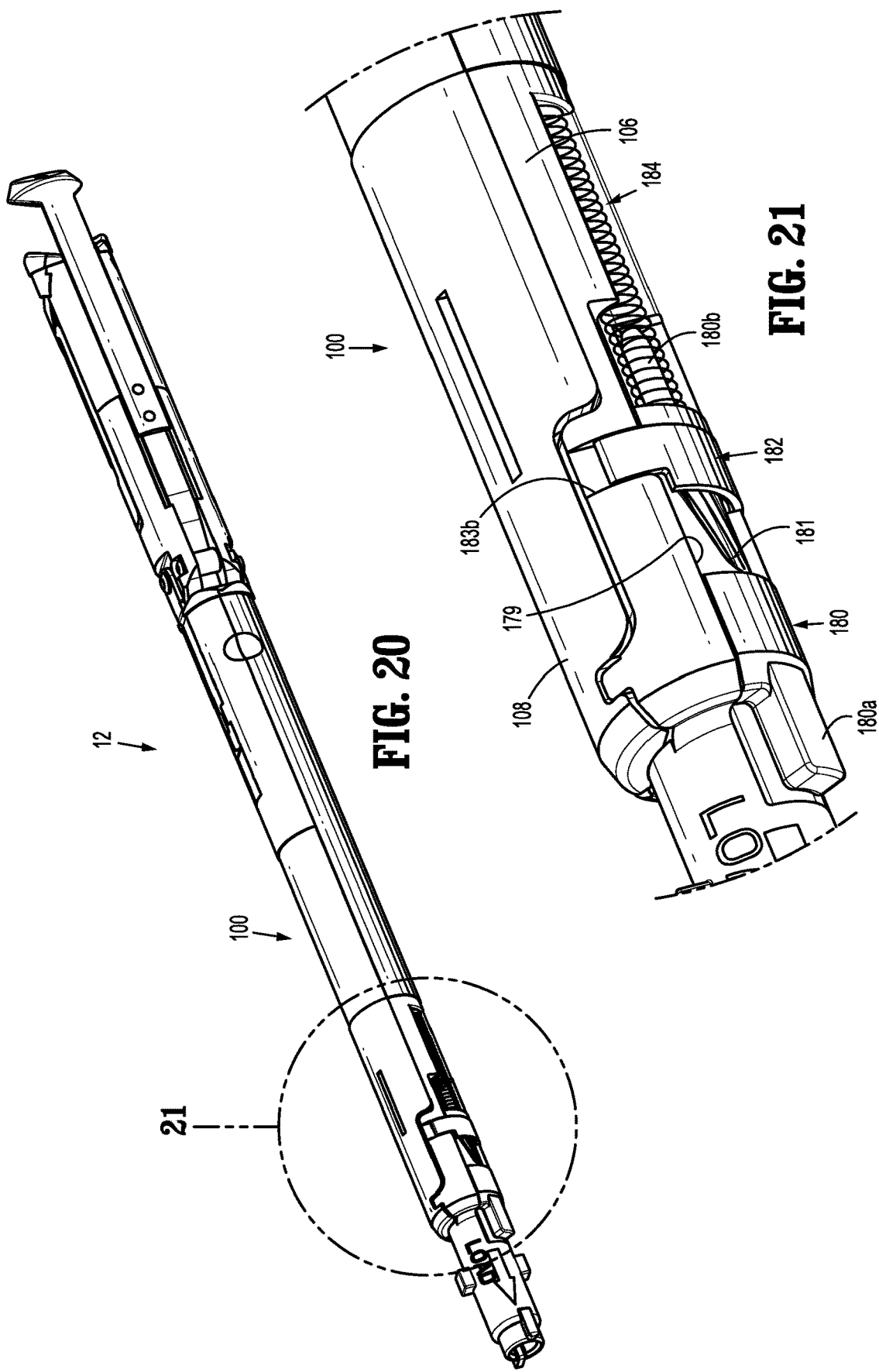

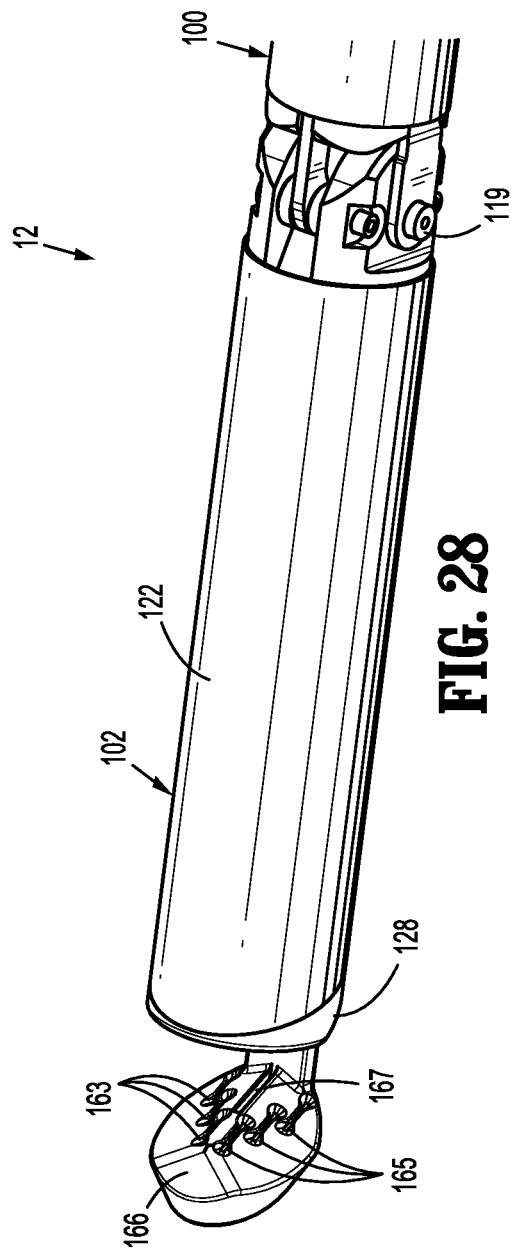
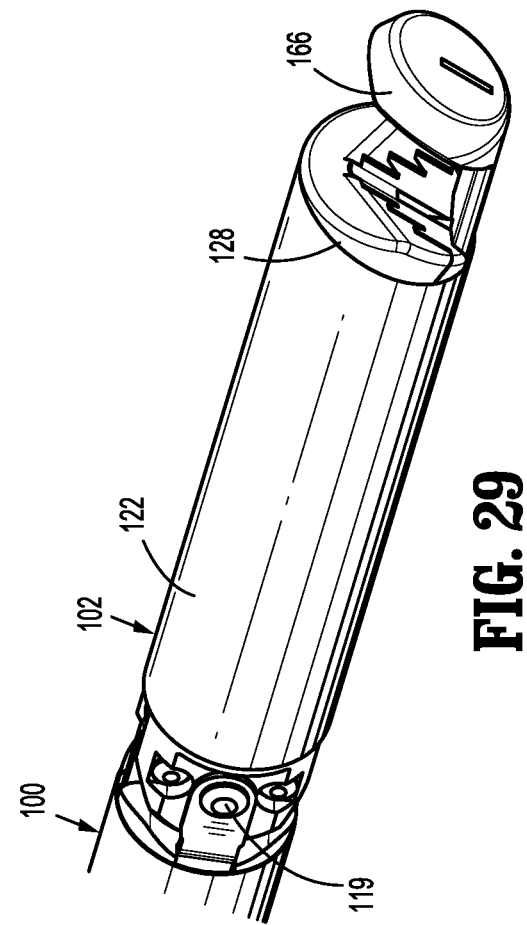

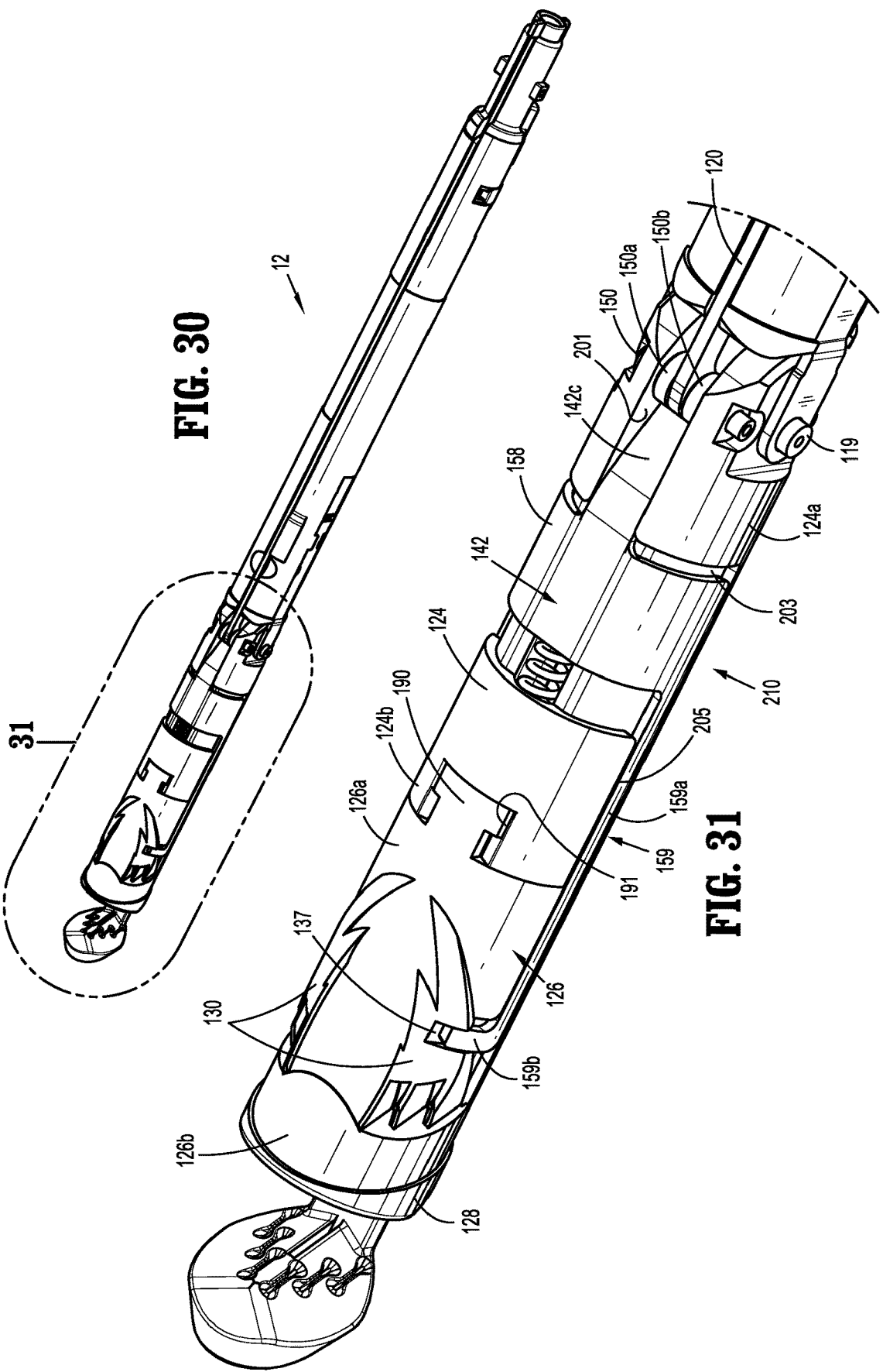

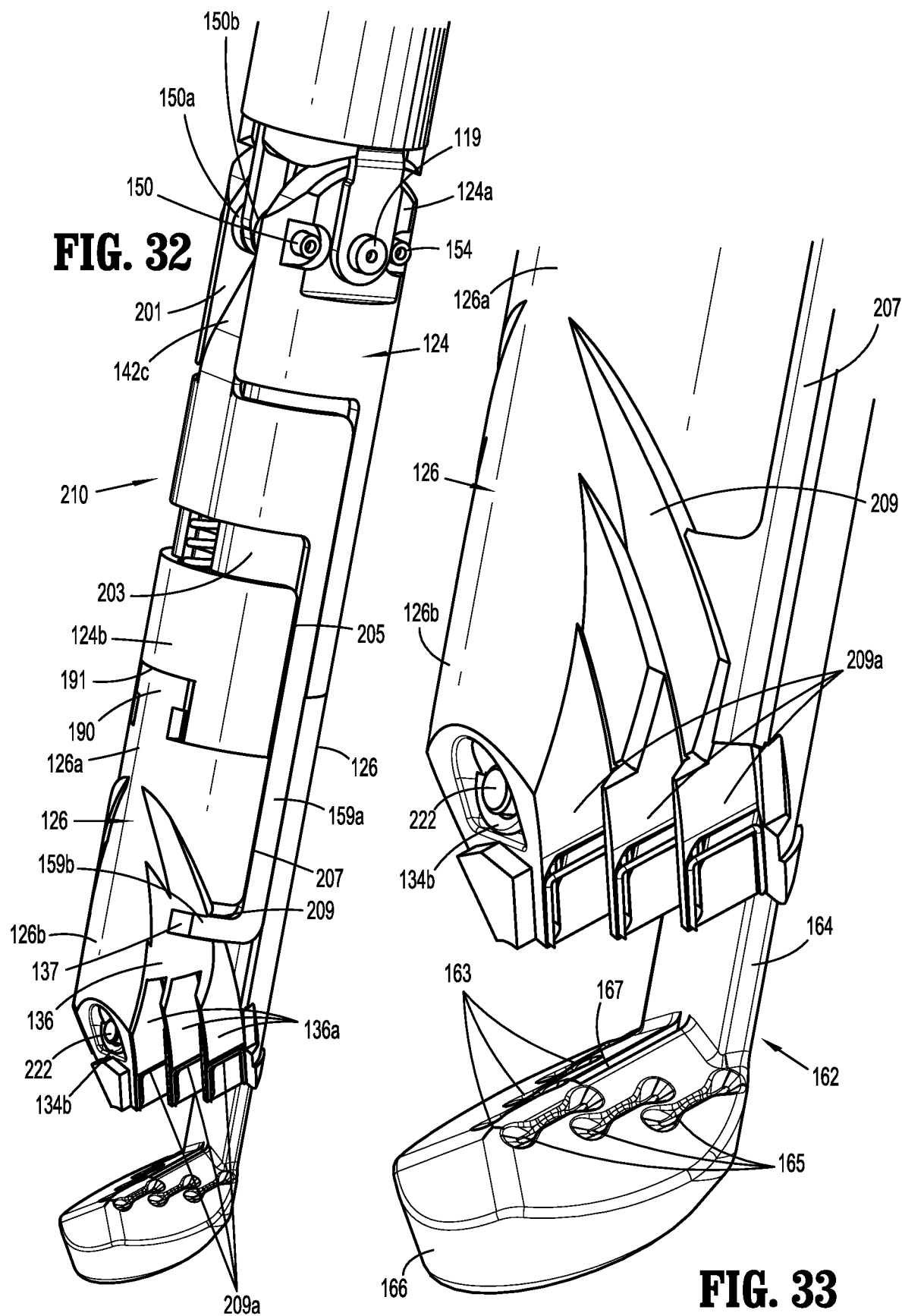

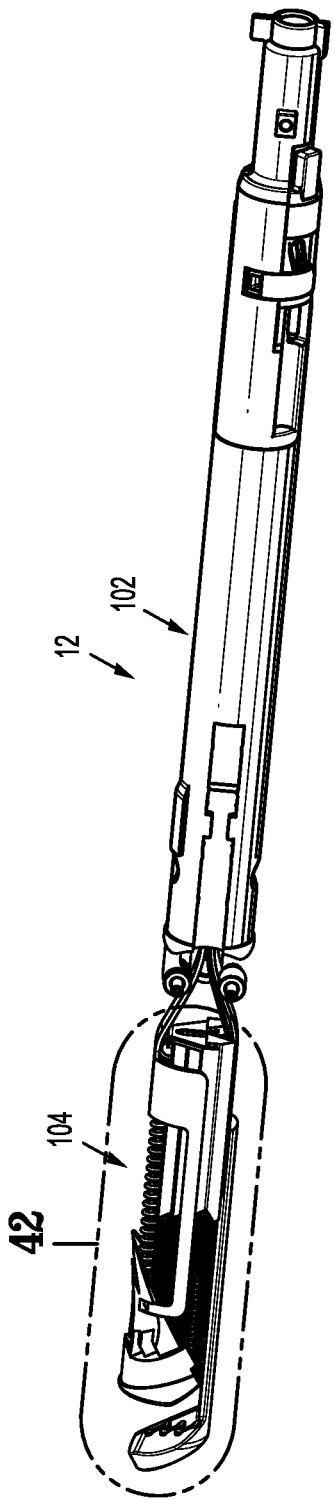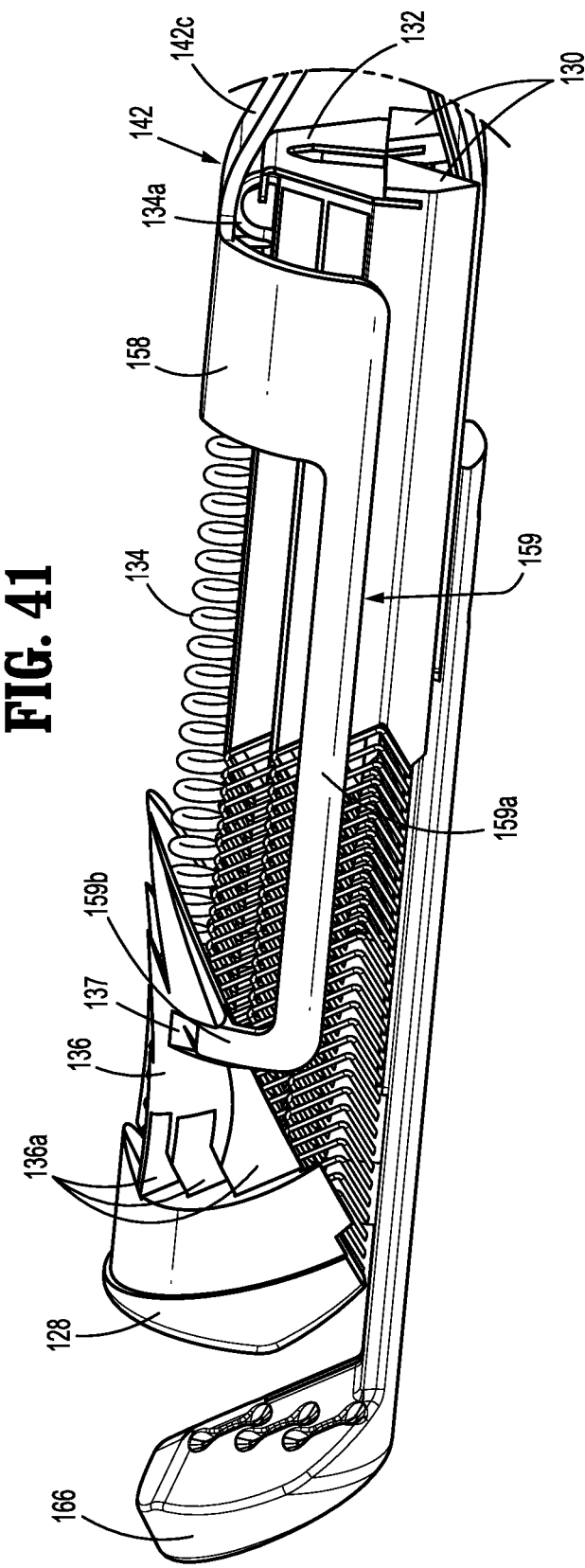
FIG. 41
FIG. 42

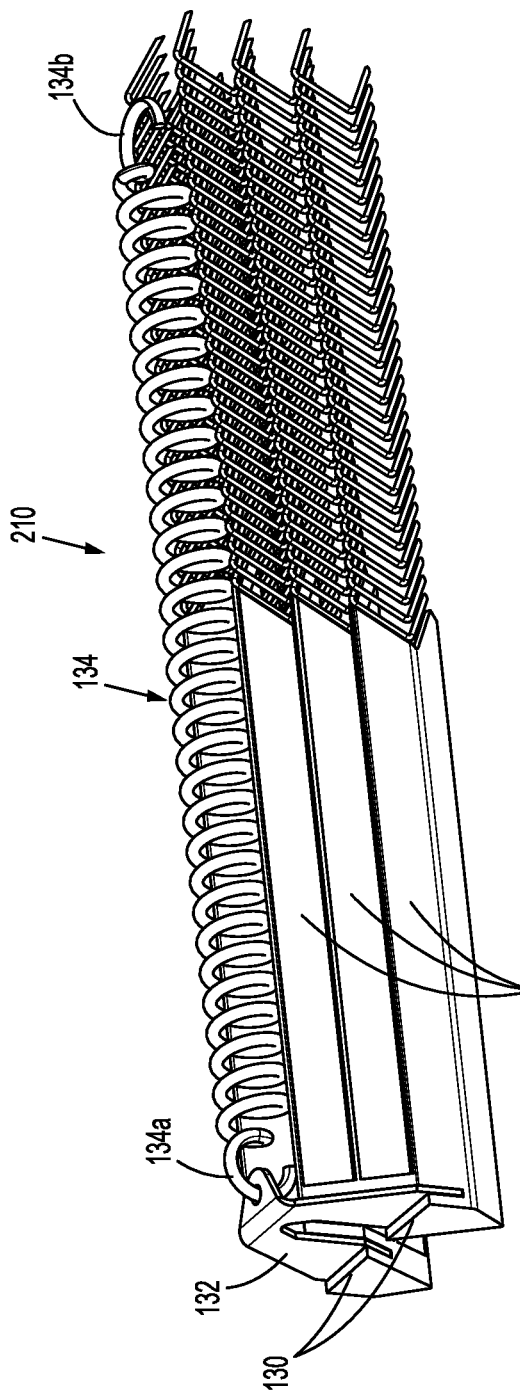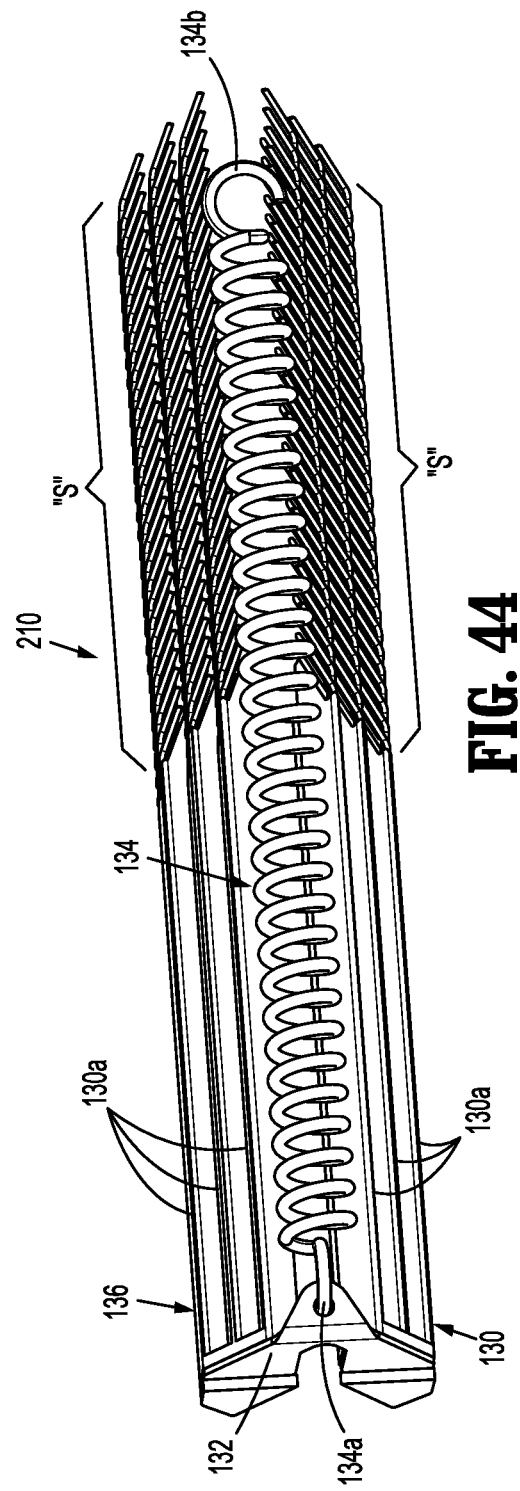

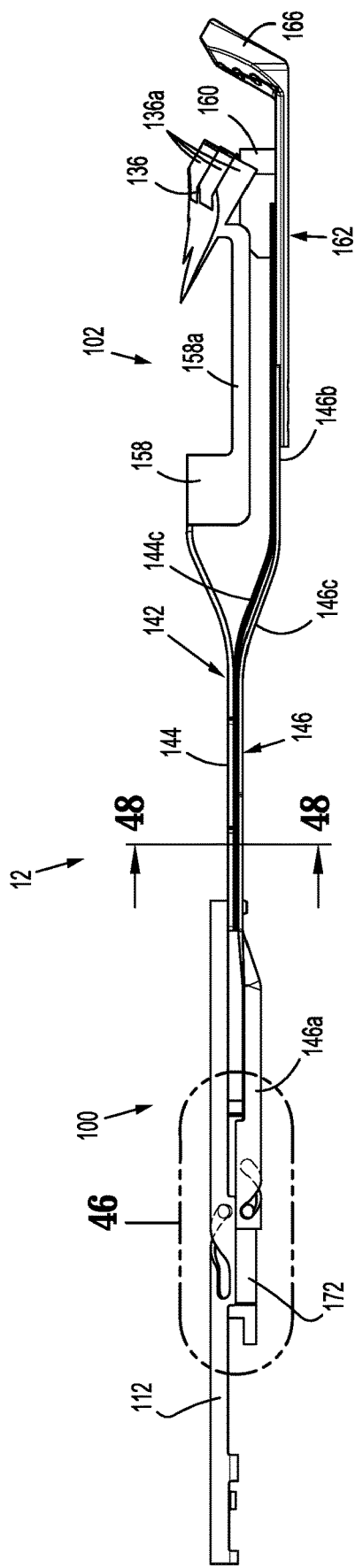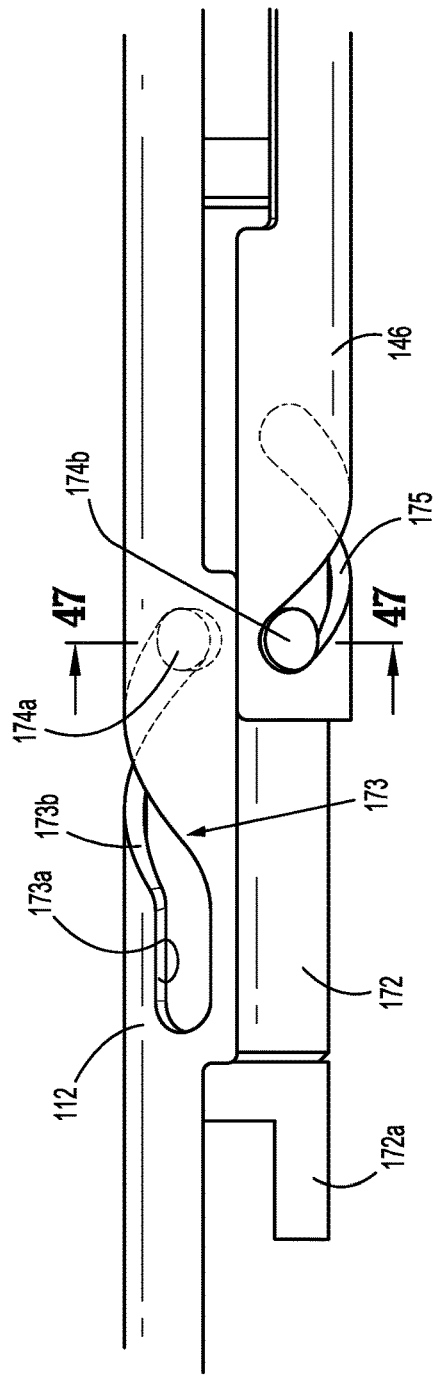
FIG. 45
FIG. 46

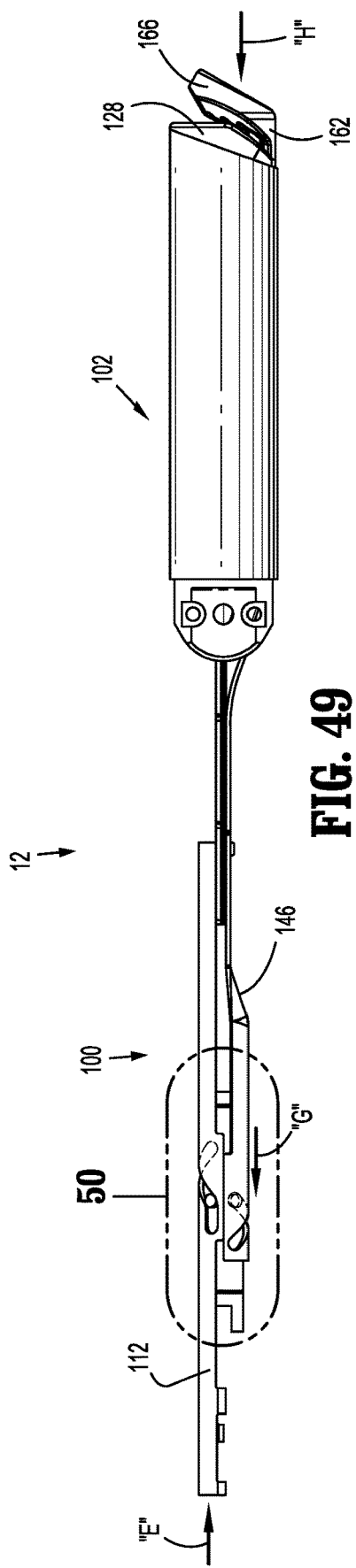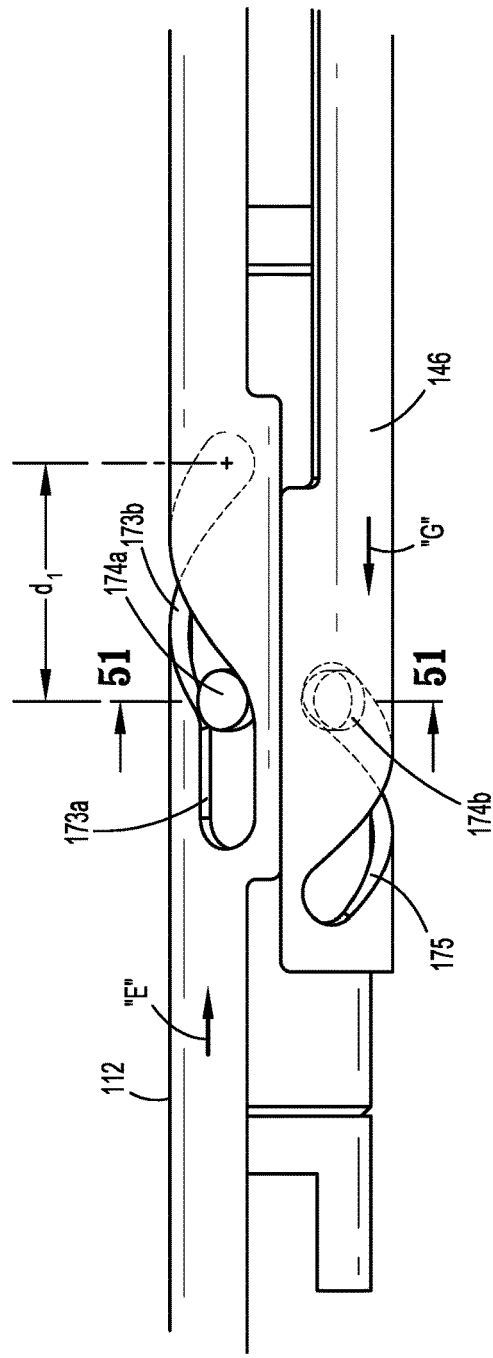
FIG. 49
FIG. 50

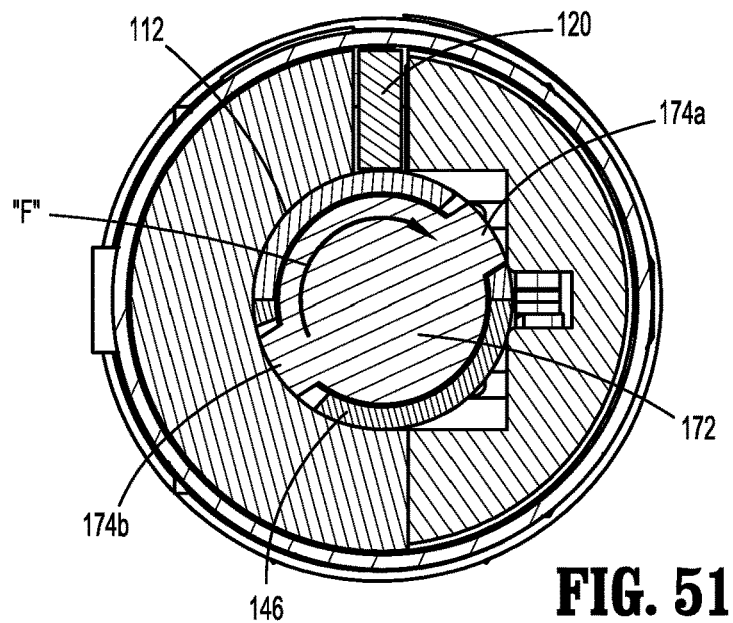
FIG. 51
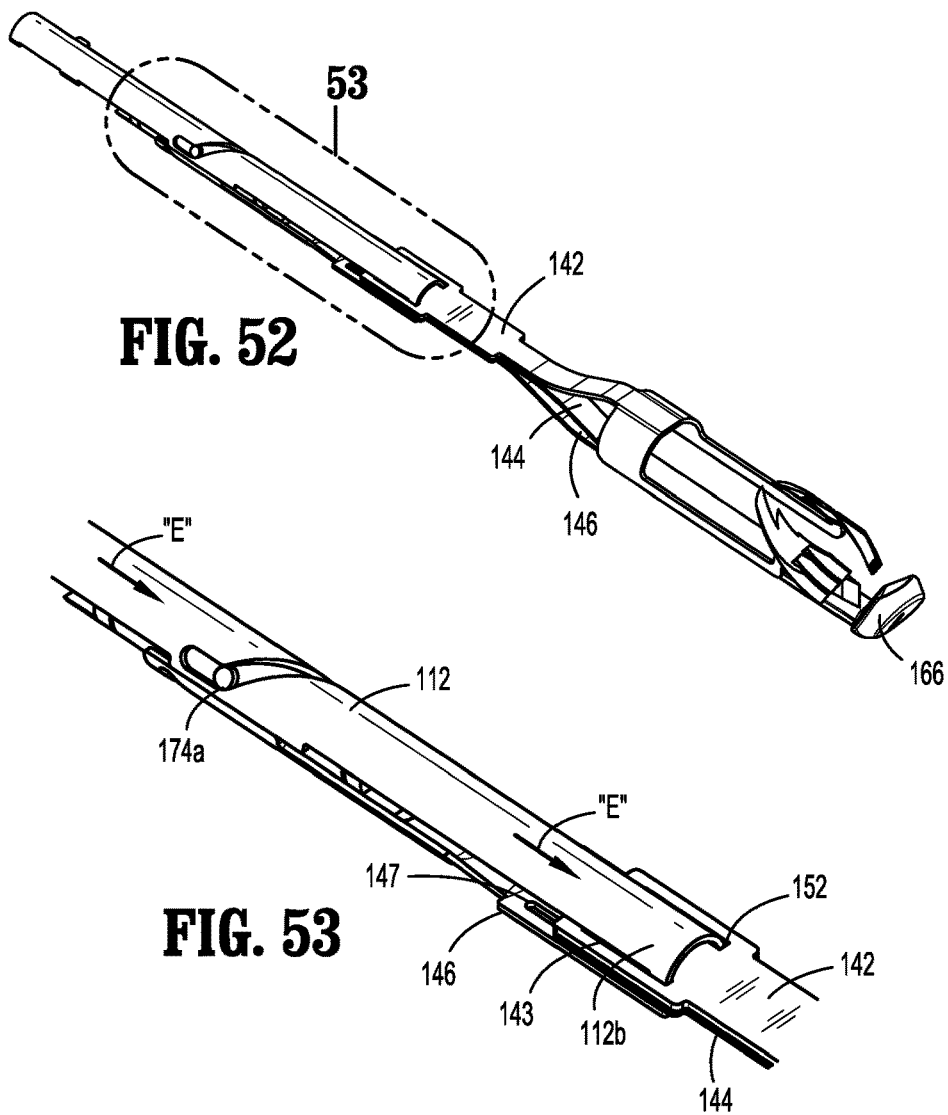
FIG. 52
FIG. 53

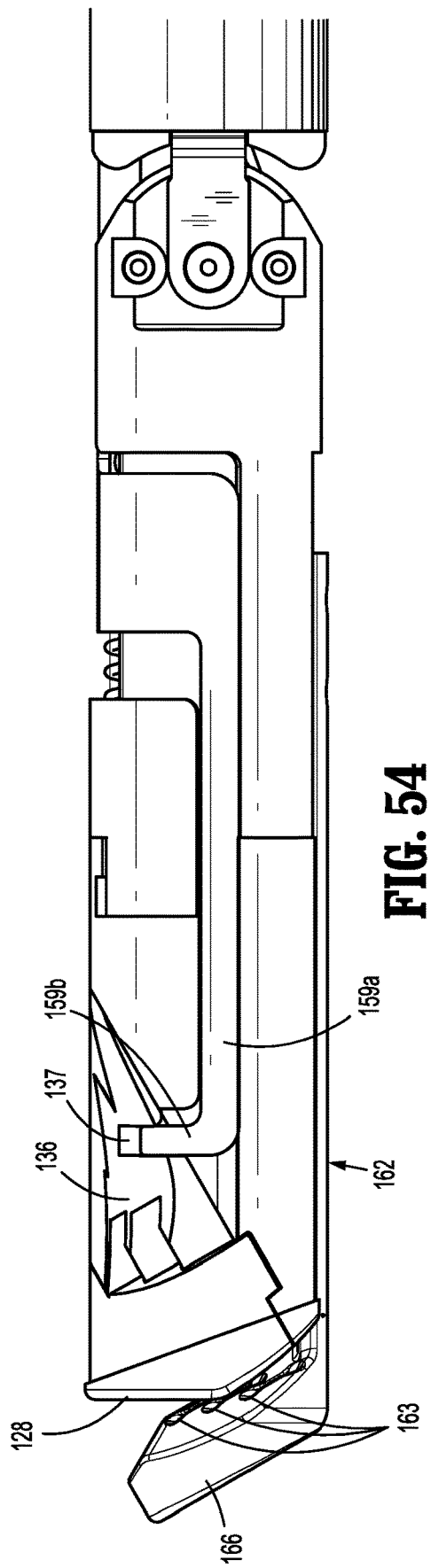
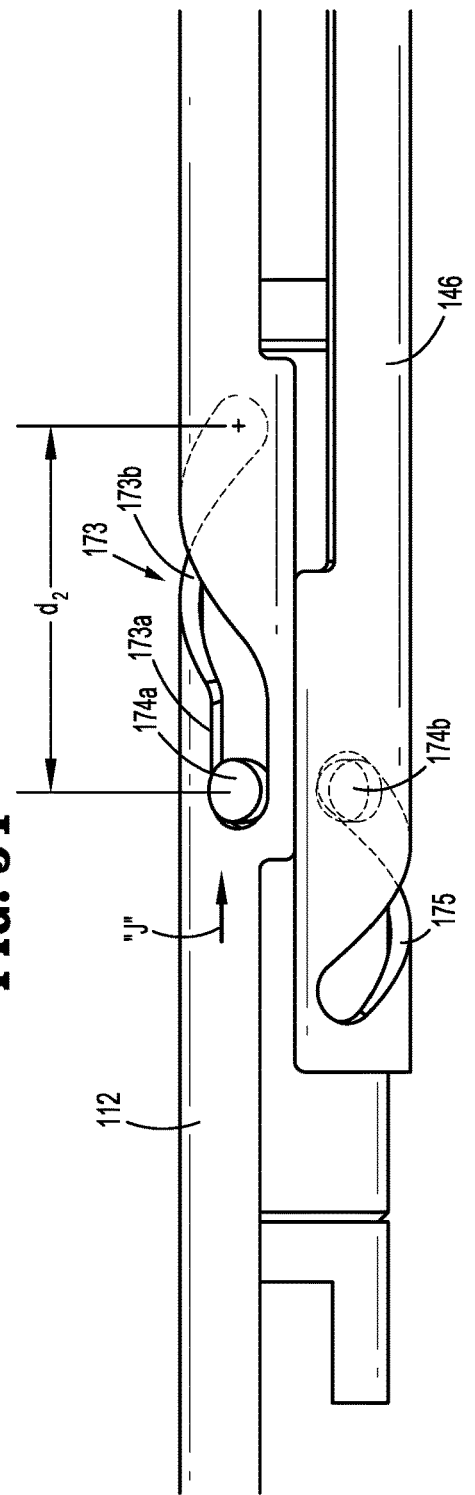

SURGICAL INSTRUMENT

CROSS-REFERENCE TO RELATED APPLICATIONS

This application is a Continuation of U.S. patent application Ser. No. 14/507,877 filed Oct. 7, 2014, which claims the benefit of and priority to U.S. Provisional Patent Application No. 61/994,155, filed May 16, 2014, the entire disclosure of which is incorporated by reference herein.

BACKGROUND

Technical Field

The present disclosure relates to surgical instruments for applying surgical staples to and cutting body tissue, and more particularly, to a surgical instrument for progressively placing rows of staples in body tissue and forming an incision between the staple rows.

Background of Related Art

Many surgical procedures require the application of one or more surgical fasteners, e.g., staples, to body organs and tissue. In many instances, the staples are secured to tissue in linear rows and the tissue is cut between the rows of staples. Typically, the tool assembly for stapling and cutting tissue is configured for a single use. In this manner, tissue to be stapled and cut is positioned between a cartridge and an anvil of the tool assembly and the tool assembly is actuated. Any further stapling and cutting of the tissue requires replacement of the staple cartridge. It would be beneficial to provide a surgical stapler that is capable of multiple actuations without having to replace the staple cartridge.

SUMMARY

A surgical stapling apparatus for progressively stapling and forming an incision in body tissue. The apparatus including a body portion and a tool assembly supported on the body portion. The apparatus further including an input cam member slidable within the body portion, a drum member rotatably supported within the body portion, and an output cam member slidable within the body portion. The drum member is coupled to the input cam member such that linear movement of the input cam member effects rotatable movement of the drum member. The output cam member is coupled to the drum member such that rotatable movement of the drum member effects linear movement of the output cam member. Linear movement of the input cam member causes linear movement of the output cam member to effect movement of an anvil in relation to a cartridge between unclamped and clamped positions.

In one embodiment, the drum member includes a first post and a second post and the input cam member and output cam member each define a slot, the first post being slidably received in the slot of the input cam member and the second post being slidably received within the slot of the output cam member. The slot of the input cam member may include a helical portion and a linear portion and the slot in the output cam member may be helical. The advancement of the input cam member may cause the first post to traverse the helical portion of the slot in the input cam member to rotate the drum member and rotation of the drum member may cause the second post to traverse the slot of the output cam member to effect linear movement of the output cam member. Receipt of the first post within the linear portion of the slot in the input cam member may permit linear movement of the input cam member without effecting rotatable movement of the drum member.

The surgical stapling apparatus may further include a pusher driver coupled to the input cam member. The pusher driver may define dwell slots and the input cam member may define tabs. The tabs may be slidably received within the dwell slots to permit linear movement of the input cam member relative to the pusher driver. In embodiments, linear advancement of the pusher driver effects corresponding movement of the input cam member after the tabs are advanced to a distal end of the dwell slots.

The surgical stapling apparatus may also include a knife driver coupled to the input cam member. The knife driver may define dwell slots and the tabs of the input cam member may be slidably received within the dwell slots to permit linear movement of the input cam member relative to the knife driver. Linear advancement of the knife driver may correspond to movement of the input cam member after the tabs are advanced to a distal end of the dwell slots.

In some embodiments, the distal end of the dwell slots of the knife driver are spaced distally from the distal end of the dwell slots of the pusher driver such that the input cam member effects advancement of the knife driver subsequent to advancing the pusher driver. Advancement of the pusher driver may staple tissue and advancement of the knife driver may cut tissue.

In addition, the surgical stapling apparatus may include a staple supply assembly supported within the tool assembly. The staple supply assembly may include a pair of pressure plates each including a plurality of extensions that engage a proximal staple in a plurality of rows of staples. The pressure plates may be biased in a distal direction by a spring. The spring may be connected to each of the pressure plates by a spring clip. Each of the pair of pressures plates may include three extensions.

Also provided is a surgical apparatus including, a body portion, a first member slidable within the body portion, a second member rotatably supported within the body portion and operably connected to the first member, and a third member slidable within the body portion and operably connected to the body portion. Linear movement of the first member effects rotational movement of the second member which effects linear movement of the third member.

The surgical apparatus may further include a fourth member slidable within the body portion, wherein linear movement of the first member effects linear movement of the fourth member. The surgical apparatus may further include a fifth member slidable within the body portion, wherein linear movement of the first member effects linear movement of the fifth member.

In addition a surgical apparatus including a body portion, a first elongate member slidable within the body portion, a second elongate member slidable within body portion and operably connected to the first elongate member, and a third elongate member slidable within the body portion and operably connected to the first member is provided. Advancement of the first elongate member a first distance effects retraction of the second elongate member and advancement of the first elongate member a second distance effects advancement of the third elongate member.

The surgical apparatus may further include a fourth elongate member slidable within the body portion and operably connected to the first elongate member. Advancement of the first elongate member a third distance effects continued advancement of the third elongate member and advancement of the fourth elongate member. The surgical apparatus may further include a cylindrical member rotatably supported within the body portion. Advancement of the first elongate member the first distance may effect rotation of the cylindrical member which effects retraction of the second elongate member.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment given below, serve to explain the principles of the disclosure, wherein:

FIG. 2 is a top view of the loading unit shown in FIG. 1;

FIG. 3 is a side view of the loading unit shown in FIG. 1;

FIG. 6A is an enlarged perspective view of a housing member, a staple cartridge, and a cartridge cover of the tool assembly shown in FIG. 7;

FIG. 6B is another perspective view of the housing member, the staple cartridge, and the cartridge cover shown in FIG. 6A;

FIG. 7 is a perspective view of a pusher assembly of the loading unit shown in FIG. 1;

FIG. 7A is an enlarged perspective view of a pusher member of the pusher assembly shown in FIG. 7;

FIG. 8 is a perspective view of a knife driver assembly of the loading unit shown in FIG. 1;

FIG. 9 is a perspective view of an anvil assembly of the loading unit shown in FIG. 1;

FIG. 14 is an enlarged view of the indicated area of detail shown in FIG. 10;

FIG. 15 is a perspective view of the loading unit shown in FIG. 1 with a sleeve of a body portion removed;

FIG. 16 is an enlarged view of the indicated area of detail shown in FIG. 15;

FIG. 17 is a perspective assembled view of the pusher assembly shown in FIG. 7, the knife driver assembly shown in FIG. 8, and the anvil assembly shown in FIG. 9 of the loading unit shown in FIG. 1;

FIG. 18 is another perspective view of the assemblies shown in FIG. 17;

FIG. 19 is another perspective view of the assemblies shown in FIG. 17;

FIG. 20 is a perspective view of a safety lock assembly of the loading unit shown in FIG. 15;

FIG. 21 is an enlarged view of the indicated area of detail shown in FIG. 20;

FIG. 28 is a perspective view of the tool assembly of the loading unit shown in FIG. 1;

FIG. 29 is another perspective view of the tool assembly of the loading unit shown in FIG. 1;

FIG. 30 is a perspective view of the loading unit shown in FIG. 1 with the outer sleeves of the body portion and the tool assembly removed;

FIG. 31 is an enlarged view of the indicated area of detail shown in FIG. 30;

FIG. 32 is a perspective side view of the tool assembly shown in FIG. 30;

FIG. 33 is an enlarged perspective view of the distal end of the tool assembly shown in FIG. 32;

FIG. 41 is a perspective side view of the loading unit shown in FIG. 1 with the outer sleeves of the body portion and tool assembly removed;

FIG. 42 is an enlarged view of the indicated area of detail shown FIG. 41;

FIG. 43 is a perspective view of a staple supply assembly of the loading unit shown in FIG. 1;

FIG. 44 is another perspective view of the staple supply assembly shown in FIG. 43;

FIG. 45 is a side view of the functional components of the loading unit shown in FIG. 1 in an unclamped position;

FIG. 46 is an enlarged view of the indicated area of detail shown in FIG. 45;

FIG. 49 is a side view of the functional components of the loading unit shown in FIG. 1 in a clamped position;

FIG. 50 is an enlarged view of the indicated area of detail shown in FIG. 49;

FIG. 51 is a cross-sectional end view of the functional components shown in FIG. 49 taken along section line 51-51 shown in FIG. 50;

FIG. 52 is a perspective view of the functional components shown in FIG. 45 in the clamped position;

FIG. 53 is an enlarged view of the indicated area of detail shown in FIG. 52;

FIG. 54 is a side view of the tool assembly shown in FIG. 1 in the clamped position;

FIG. 55 is the view of the functional components shown in FIG. 50 in an fully-actuated position;

DETAILED DESCRIPTION

Figure 1:
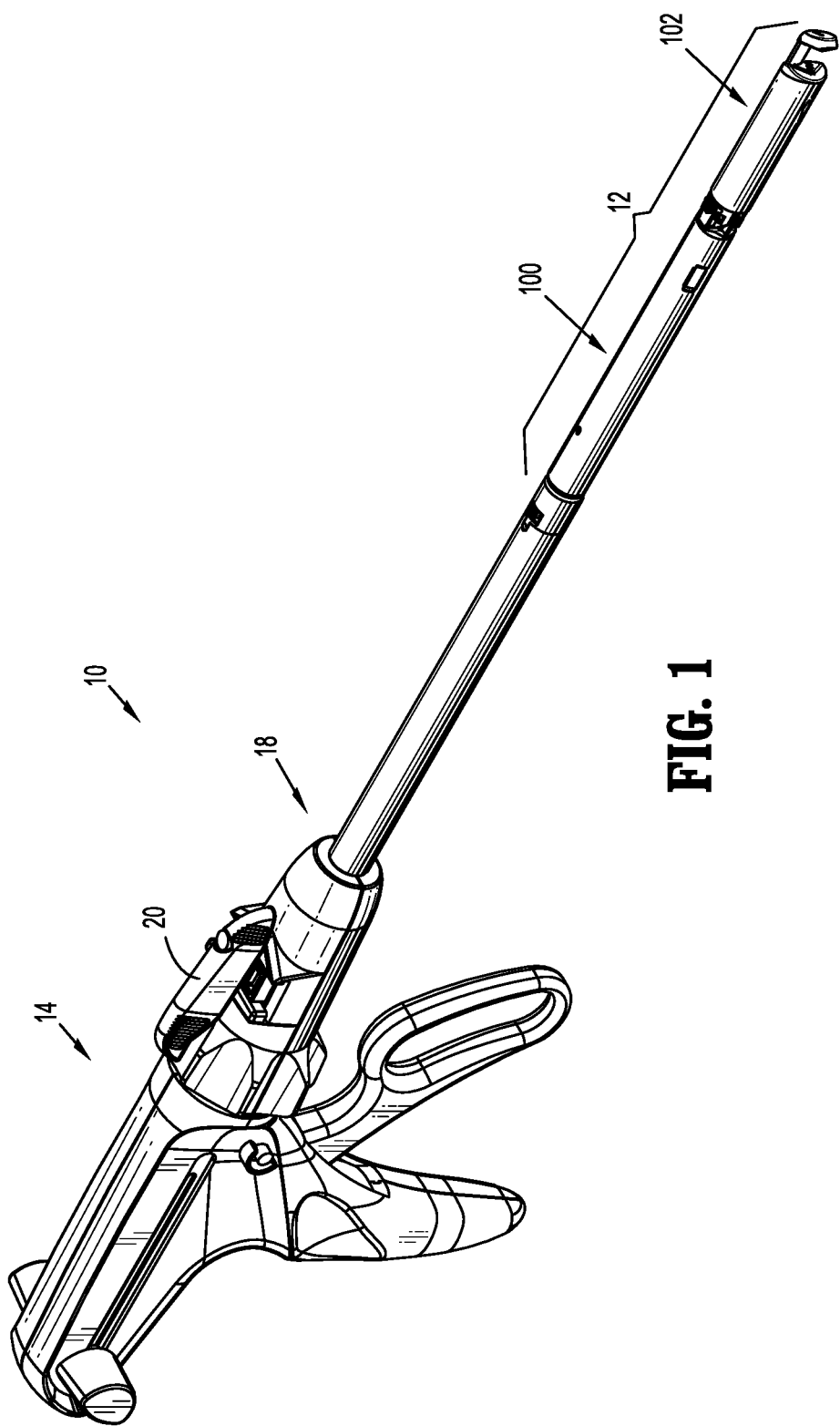
FIG. 1 is a perspective view of a surgical stapler including a loading unit according to an embodiment of the present disclosure.

Embodiments of the presently disclosed surgical stapling apparatus will now be described in detail with reference to the drawings in which like reference numerals designate identical or corresponding elements in each of the several views. Throughout this description, the term "proximal" will refer to the portion of the apparatus closest to the user and the term "distal" will refer to the portion of the apparatus farthest from the user.

With reference initially to FIG. 1, a surgical instrument for applying surgical staples to body tissue is shown generally as surgical stapler 10. Surgical stapler 10 is configured to cut and fasten body tissue. In particular and as will be described in further detail below, surgical stapler 10 is configured to progressively apply a plurality of surgical fasteners to tissue while progressively forming an incision in the fastened tissue during an endoscopic procedure. Although shown and described as relating to a surgical instrument for applying surgical staples to body tissue, the aspects of the present disclosure may be modified for use in other surgical instruments, e.g., surgical forceps, mesh deployment devices.

Surgical stapler 10 includes a loading unit 12 for fastening and cutting tissue and an actuation unit 14 for controlling and actuating the loading unit 12. As shown, the actuation unit 14 includes a handle assembly 16 configured for operable engagement by a user and for manual actuation of loading unit 12. An elongated body portion 18 extends from handle assembly 16 and is configured to operably connect loading unit 12 to handle assembly 16. It is envisioned that loading unit 12 may be configured for operation with actuation units having alternate configurations. For example, the actuation unit may include a powered handle assembly or robotic system. In other embodiments, loading unit 12 may be integrally formed with actuation unit 14. For a detailed description of an exemplary actuation unit for controlling and actuating loading unit 12, please refer to commonly owned U.S. Pat. No. 6,330,965, the content of which is incorporated by reference herein in its entirety.

With reference now to FIGS. 1-6, loading unit 12 of surgical stapler 10 includes a body portion 100 and a tool assembly 102 pivotally connected to body portion 100. The body portion 100 of the loading unit 12 is configured to be releasably coupled to elongated body portion 18 of actuation unit 14. Although shown as being configured for bayonet coupling, it is envisioned that loading unit 12 may be modified for connection with elongated body portion 18 of actuation unit 14 in any suitable manner.

Figure 5:
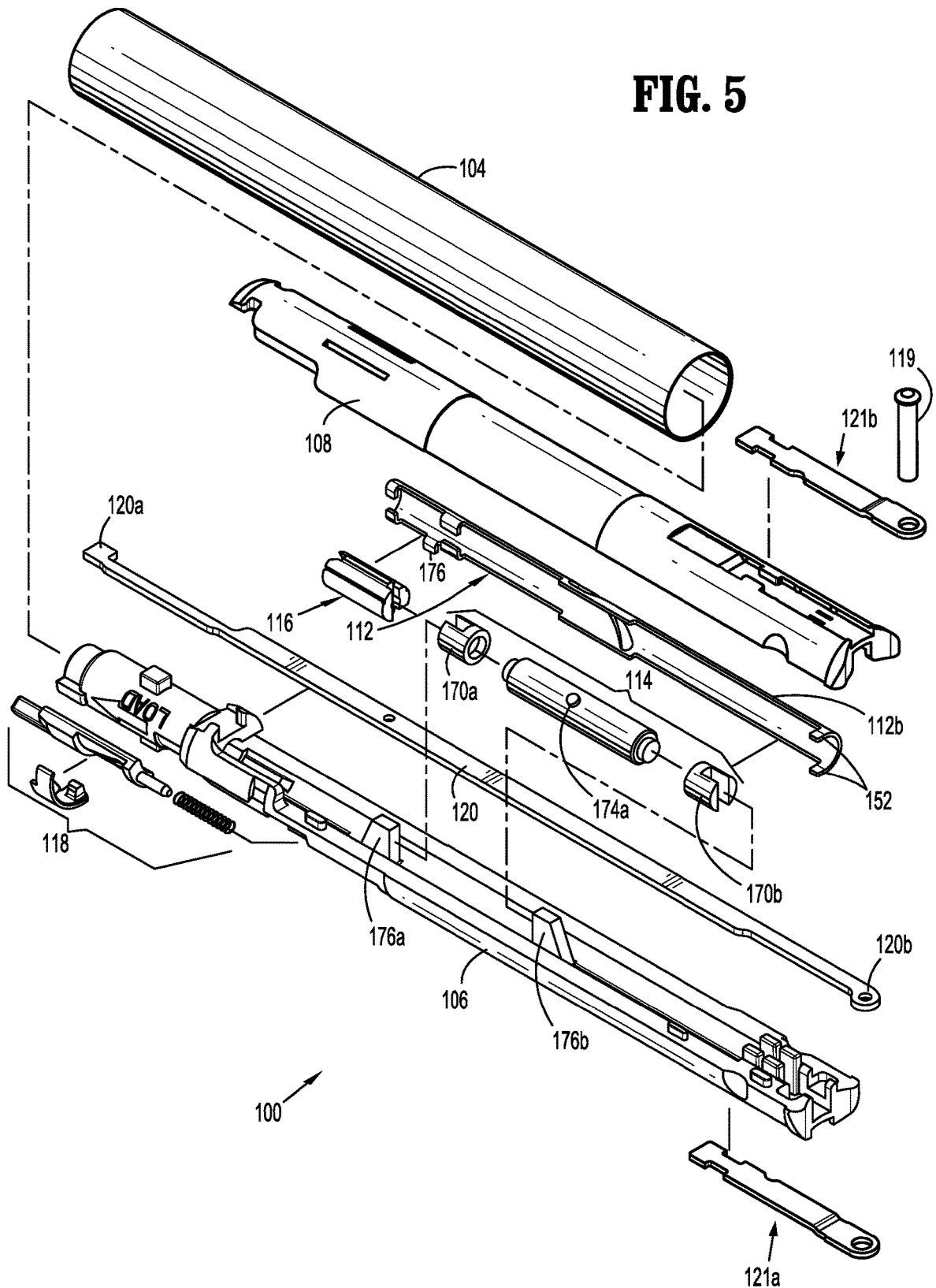
FIG. 5 is an exploded perspective view of the body portion of the loading unit shown in FIG. 1.

With particular reference now to FIG. 5, body portion 100 of loading unit 12 includes an outer sleeve 104 which receives first and second housing halves 106, 108, an input cam bar 112, and a drum assembly 114. As will be described in further detail below, input cam bar 112 is slidably received within first and second housing halves 106, 108 and drum assembly 114 is rotatably mounted within first and second housing halves 106, 108. Input cam bar 112 and drum assembly 114 are configured to effect actuation of tool assembly 102 of loading unit 12 during operation of surgical stapler 10 (FIG. 1), as will be described in further detail below.

With continued reference to FIG. 5, body portion 100 of loading unit 12 further includes a drive member 116, a safety lock assembly 118, and an articulation rod 120. As will be described in further detail below, drive member 116 is configured for operable engagement with a drive member (not shown) of actuation unit 14 (FIG. 1) such that operation of the actuation unit 14 effects operation of the tool assembly 102, as will be discussed in detail below. Safety lock assembly 118 is configured to prevent actuation of loading unit 12 until loading unit 12 is secured to elongated body portion 18 (FIG. 1) of actuation unit 14 (FIG. 1), and articulation rod 120 is configured to effectuate articulation of tool assembly 102 relative to body portion 100.

Operation of the safety lock assembly 118 is described in commonly owned U.S. Pat. No. 8,469,254, the content of which is incorporated herein by reference in its entirety. A first connecting element 121a extends from a distal end of first housing half 106 and a second connecting element 121b extends from a distal end of second housing half 108. First and second connecting elements 121a, 121b are coupled about a pivot pin 119 to pivotally secure tool assembly 102 to body portion 100.

Figure 6:
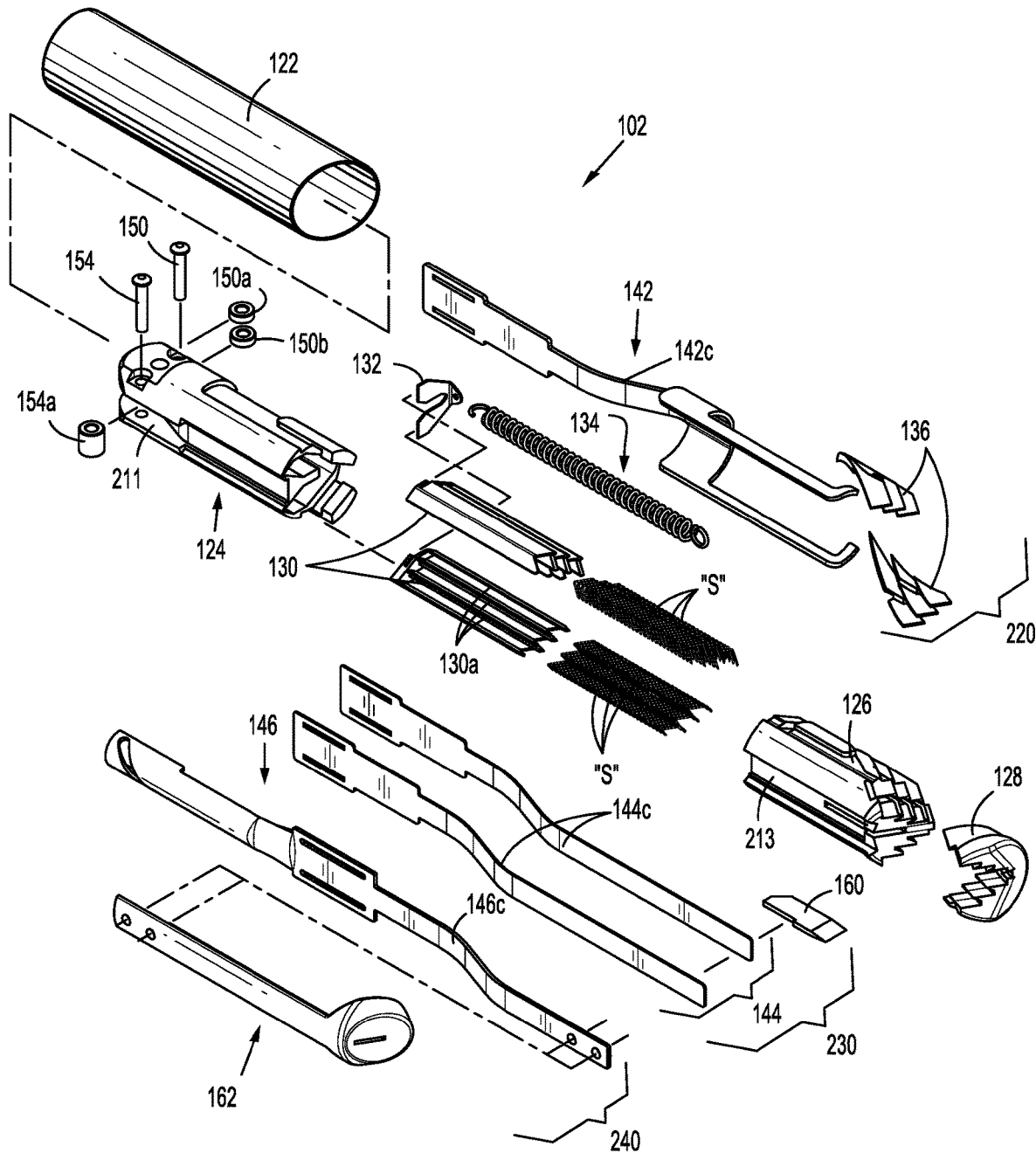
FIG. 6 is an exploded perspective view of a tool assembly of the loading unit shown in FIG. 1.
Figure 10:
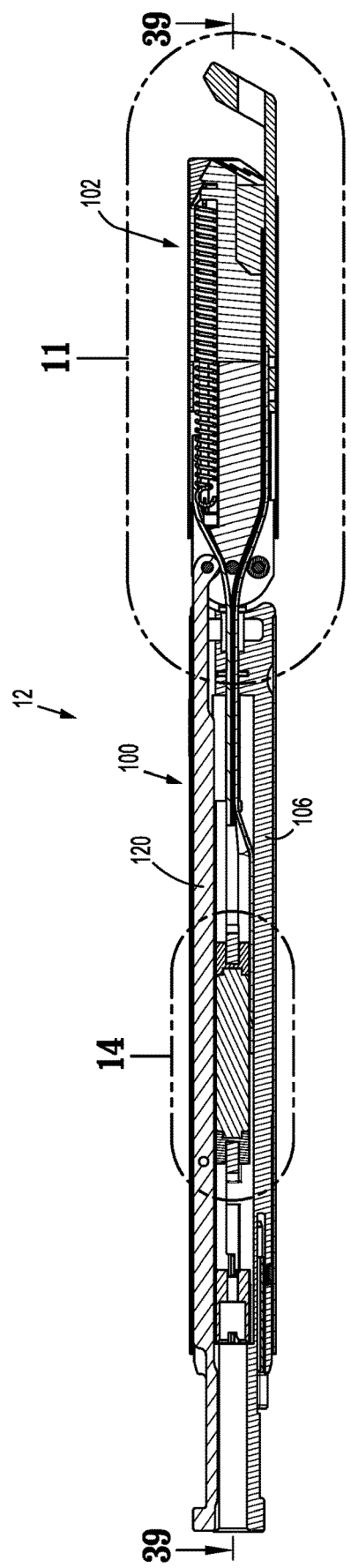
FIG. 10 is a cross-sectional view of the loading unit shown in FIG. 1 taken along section line 10-10 in FIG. 2.
Figure 11:
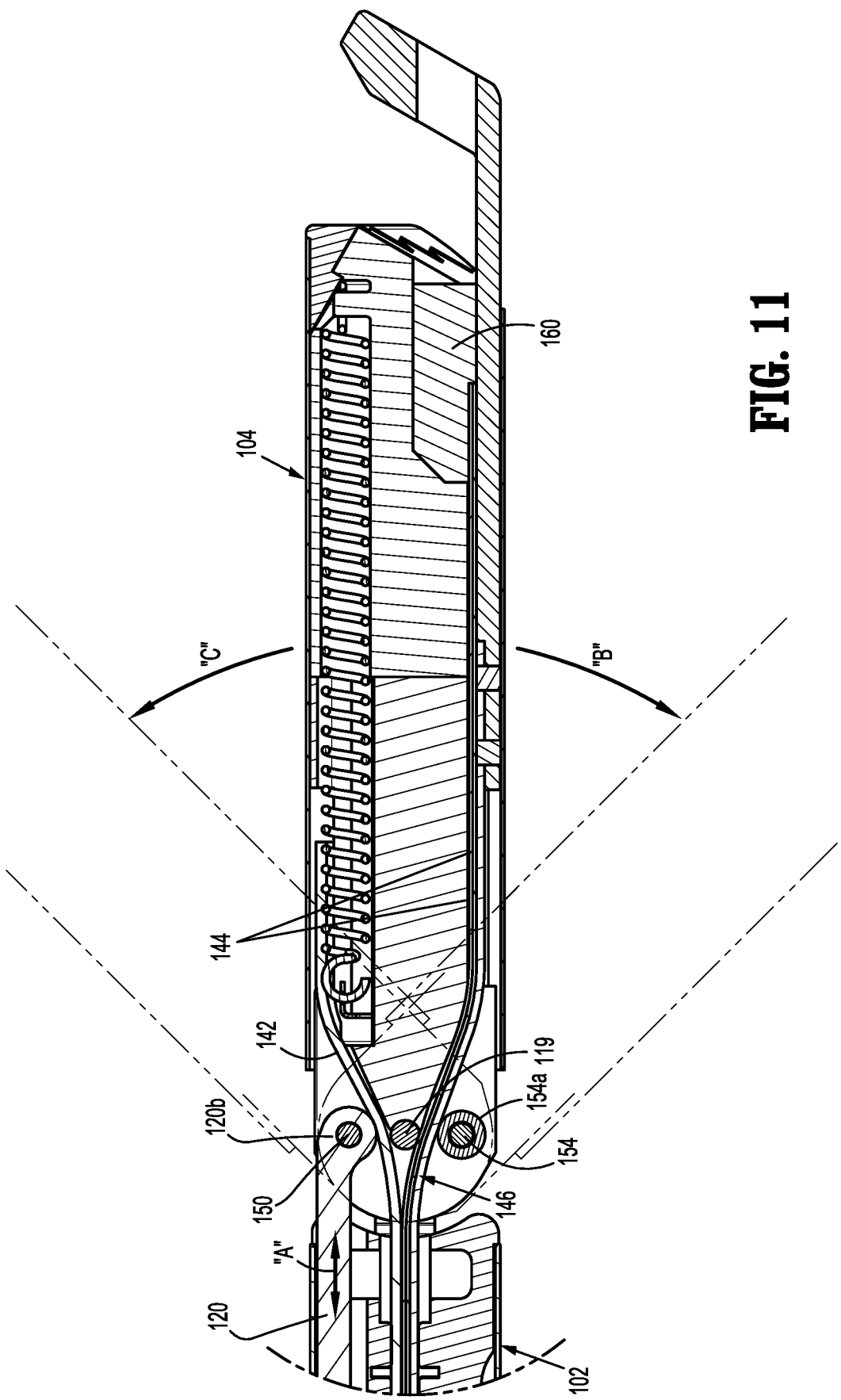
FIG. 11 is an enlarged view of the indicated area of detail shown in FIG. 10.
Figure 12:
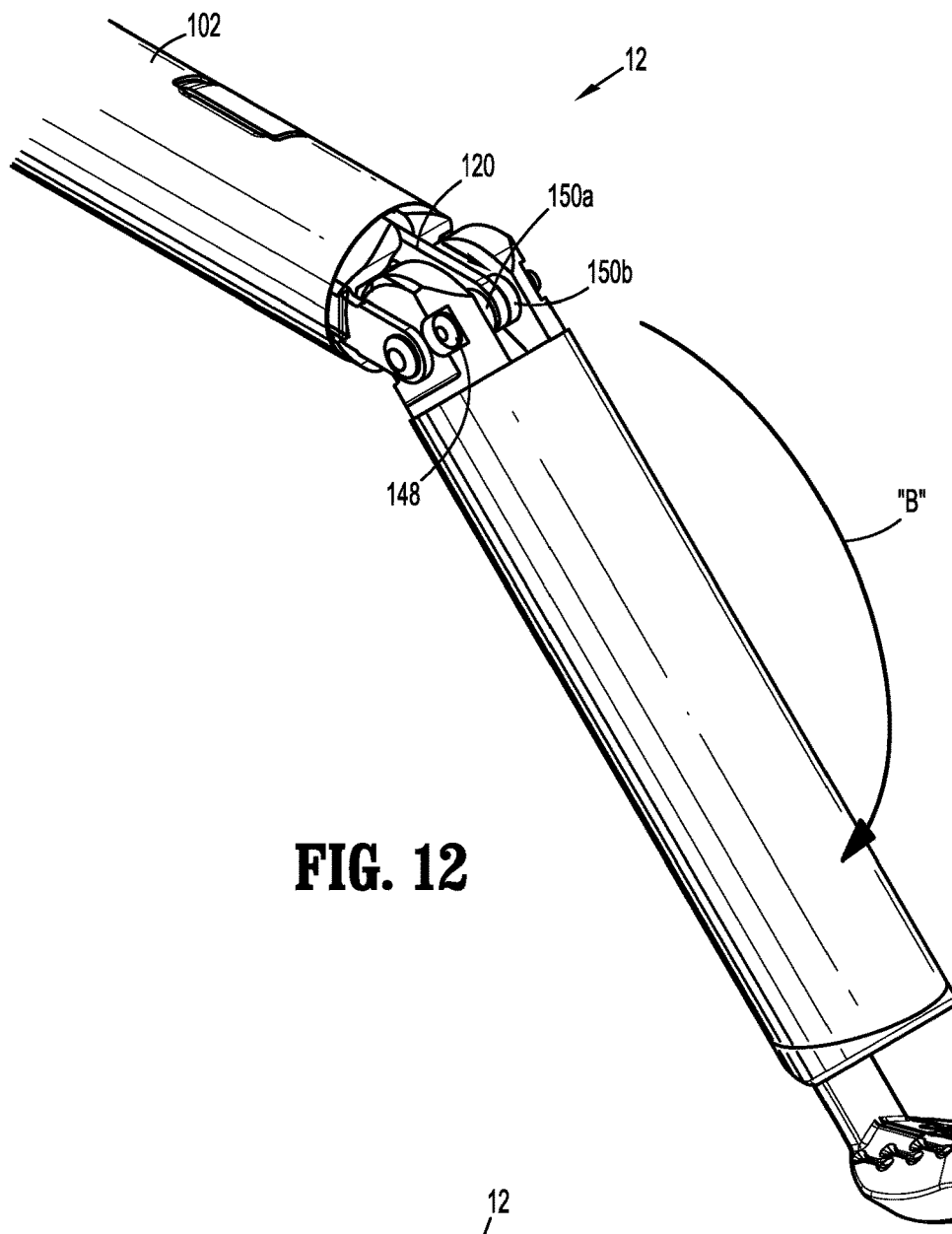
FIG. 12 is a perspective view of the tool assembly of the loading unit shown in FIG. 1 in a first articulated position.
Figure 13:
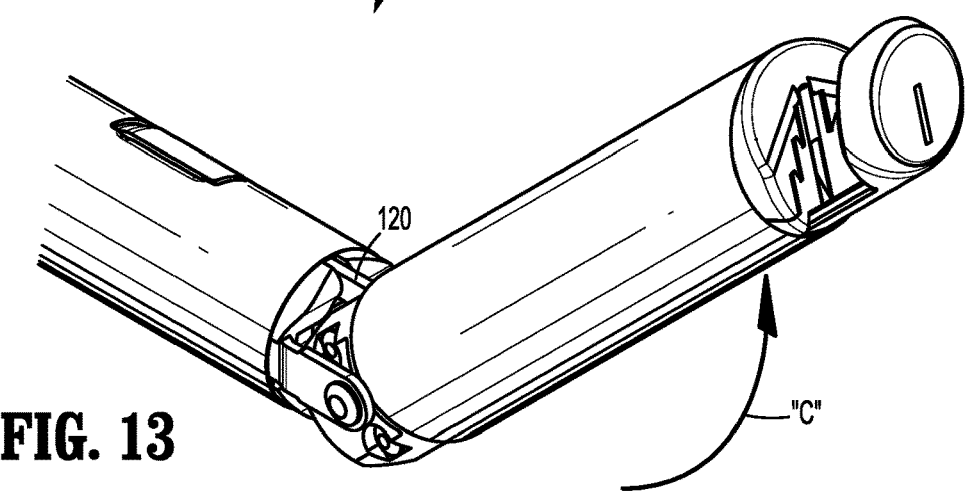
FIG. 13 is a perspective view of the tool assembly of the loading unit shown in FIG. 1 in a second articulated position.

With reference now to FIG. 6 tool assembly 102 of loading unit 12 includes an outer sleeve 122 configured to receive a housing member 124 and a staple cartridge 126. Staple cartridge 126 is configured to be capped by a cartridge cover 128. Tool assembly 102 further includes a pair of pressure plates 130, a spring clip 132, a spring 134, and a pair of pusher members 136. As will be described in further detail below, pressure plates 130, spring clip 132, and spring 134 operate within housing member 124 and staple cartridge 126 as a staple supply assembly 210 for supplying staples "S" to pusher members 136. Each pressure plate 130 includes a plurality of extensions 130a each configured for engaging proximal staple in a row of staples. Each extension 130a includes a substantially C-shaped cross-section corresponding to the shape of staple "S".

As will be described in further detail below, a pusher driver 142, a pair of knife drivers (referred to collectively as knife driver 144), and an output cam bar 146 extend from body portion 100 (FIG. 4) of loading unit 12 into tool assembly 102. Each of pusher driver 142, knife driver 144, and output cam bar 146 includes a flexible portion 142c, 144c, 146c, respectively, to facilitate articulated of the tool assembly 102 in relation to body portion 100. Pusher driver 142 is slidably secured relative to housing member 124 of tool assembly 102 by a first securement pin 150 and a pair of bearing rings 150a, 150b as will be described in further detail below. Knife drivers 144 and output cam bar 146 are slidably secured relative to housing member 124 of tool assembly 102 by a second securement pin 154 and a bearing ring 154a as will be described in further detail below.

With particular reference now to FIGS. 6A and 6B, a proximal end 124a of housing member 124 defines a first longitudinal channel 201 (FIG. 6B) which communicates with a semi-annular cutout 203. A distal end 124b of housing member 124 further defines a pair of longitudinal cutouts 205 which communicate with semi-annular cutout 203. Housing member 124 further defines a second longitudinal channel 211 (FIG. 6A) having an inner portion 211a and an outer portion 211b extending along the length of housing member 124. Housing member 124 also defines first and second internal channels 215a, 215b and a circular bore 221 (FIG. 6A).

With reference still to FIGS. 6A and 6B, a proximal end 126a of staple cartridge 126 defines a pair of longitudinal cutouts 207 which align with longitudinal cutouts 205 formed in distal end 124b of housing member 124 when housing member 124 and staple cartridge 126 are assembled. A distal end 126b of staple cartridge 126 defines a pair of cutouts 209 which communicate with longitudinal cutouts 207. A distal end 126b of staple cartridge 126 also defines a plurality of notches 209a. Staple cartridge 126 further defines a longitudinal channel 213 having inner and outer portions 213a, 213b corresponding to inner and outer portions 211a, 211b of second longitudinal channel 211 of housing member 124. In addition, distal end 126b of staple cartridge 126 defines a longitudinally extending slot 213c (FIG. 6A). Staple cartridge 126 also defines first and second sets of slots 217 (FIG. 6B), 219 (FIG. 6A) which communicate with first and second internal channels 215a, 215b, respectively, of housing member 124. Distal ends of first and second set of slots 217, 219 are aligned with notches 209a (FIG. 32) formed in distal end 126b of staple cartridge 126. Staple cartridge 126 further defines a circular bore 221a (FIG. 6A) which communicates with circular bore 221 of housing member 124 when staple cartridge 126 is secured to housing member 124.

As will be discussed in further detail below, housing member 124 and staple cartridge 126 operate to receive distal ends of pusher driver 142, knife driver 144, and output cam bar 146

With reference now to FIG. 7, pusher members 136 and pusher driver 142 are components of a pusher assembly 220. A proximal end 142a of pusher driver 142 defines a pair of dwell slots 143. As will be described in further detail below, dwell slots 143 of pusher driver 142 slidably receive tabs 152 (FIG. 5) formed on a distal end 112b of input cam bar 112 (FIG. 5) to permit movement of input cam bar 112 relative to pusher assembly 220. A distal end 142b of pusher driver 142 includes a semi-annular flange 158. A pair of L-shaped engagement members 159 extends from semi-annular flange 158. Engagement members 159 each include an elongated portion 159a extending from semi-annular flange 158 and an engagement portion 159b engaged with pusher members 136. More particularly, pusher members 136 each include a groove 137 which receives engagement portion 159b of engagement members 159 to secure the pusher member 136 to the pusher driver 142. Pusher driver 142 includes flexible portion 142c which extends between body portion 100 and tool assembly 102 of loading unit 12.

Flexible portion 142c permits flexion of pusher driver 142 when the tool assembly is actuated in an articulated position relative to body portion 100.

Turning now to FIG. 8, knife driver 144 together with a knife 160 forms a knife assembly 230. A proximal end 144a of knife driver 144 defines dwell slots 145. As will be described in further detail below, dwell slots 145 of knife driver 144 slidably receive tabs 152 (FIG. 5) of input cam bar 112 to permit movement of input cam bar 112 relative to knife assembly 230. Knife 160 is securely mounted to a distal end 144b of knife driver 144 by welding, an adhesive, and a mechanical fastener or in any other suitable manner. Knife driver 144 includes flexible portion 144c which is received between body portion 100 and tool assembly 102 of loading unit 12. Flexible portion 144c permits flexion of knife driver 144 when the tool assembly 102 is actuated in an articulated position relative to body portion 100.

Referring now to FIG. 9, output cam bar 146 together with an anvil member 162 forms an anvil assembly 240. Similar to pusher driver 142 and knife driver 144, output cam bar 146 defines dwell slots 147. As will be described in further detail below, dwell slots 147 of output cam bar 146 slidably receive tabs 152 (FIG. 5) of input cam bar 112 to permit movement of input cam bar 112 relative to anvil assembly 240. Anvil member 162 includes an extension portion 164 which is fixedly secured to a distal end 146b of output cam bar 146 and an anvil portion 166 disposed on extension portion 164. Anvil portion 166 of anvil member 162 defines first and second sets of staple forming pockets 163, 165 and a knife receiving pocket 167 (FIG. 28) which is positioned between the first and second set of staple forming pockets 163, 165. Output cam bar 146 includes a flexible portion 146c which extends between body portion 100 and tool assembly 102 of loading unit 12 and permits flexion of output cam bar 146 when the tool assembly 102 is actuated in an articulated position relative to body portion 100.

With reference now to FIGS. 10-13, articulation rod 120 of loading unit 12 extends along a length of body portion 100 and is operably connected at is distal end 120b to first securement pin 150 (FIG. 11) adjacent a proximal end of tool assembly 102. A proximal end 120a of articulation rod is positioned to engage an articulation mechanism (not shown) of the actuation unit 14. See, e.g., U.S. Pat. No. 8,469,254, the content of which was previously incorporated by reference herein in its entirety. 120 Movement of articulation rod 120 relative to body portion 100, as indicated by arrow "A" in FIG. 11, causes articulation of tool assembly 102 relative to body portion 100 about pivot pin 119. In particular, advancement of articulation rod 120 distally relative to body portion 100 causes articulation of tool assembly 102 in a first direction, as indicated by arrow "B" in FIG. 12, about pivot pin 119 and retraction of articulation rod 120 proximally relative to body portion 100 causes articulation of tool assembly 102 in a second direction, as indicated by arrow "C" in FIG. 13, about pivot pin 119. In one embodiment, and as shown in the drawings, advancement and retraction of articulation rod 120 is accomplished with lever 20 (FIG. 1) operably supported on elongated body portion 18 (FIG. 1) of actuation unit 14 (FIG. 1).

Figure 4:
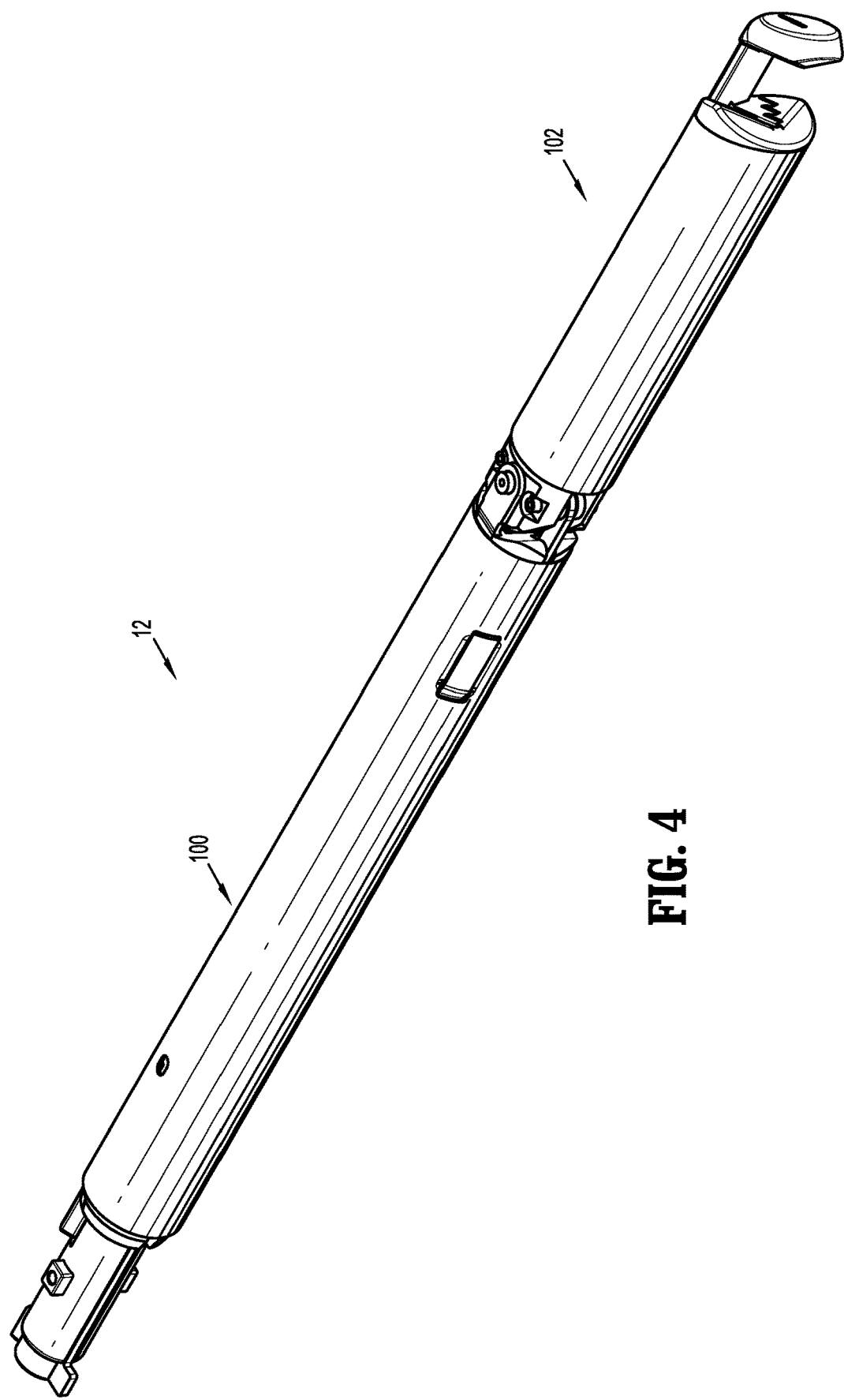
FIG. 4 is a perspective view of loading unit shown in FIG. 1.

Referring now to FIGS. 5 and 14-19, drum assembly 114 of loading unit 12 is mounted between first and second housing halves 106, 108 of body portion 100 for rotary movement and includes first and second drum bearings 170a, 170b and a drum member 172. First and second drum bearings 170a, 170b are secured to respective first and second support features 176a, 176b (FIG. 5) formed on first housing half 106 such that drum member 172 is rotatable relative to input cam bar 112 and output cam bar 146 (FIG. 4). Drum member 172 includes first and second drum posts 174a (FIG. 17), 174b (FIG. 18). First drum post 174a is received within a slot 173 (FIG. 19) of input cam bar 112 and second drum post 174b is received within a slot 175 (FIG. 18) of output cam bar 146. Slot 173 in input cam bar 112 includes a longitudinally extending proximal portion 173a and a helical distal portion 173b. Slot 175 in output cam bar 146 is helical.

As will be described in further detail below, the configuration of slot 173 in input cam bar 112 and the configuration of slot 175 in output cam bar 146 and the position of first and second drum posts 174a, 174b within respective slots 173, 175 is such that advancement of input cam bar 112 in a distal direction the housing halves 106, 108 causes rotation of drum member 172 in a first direction and rotation of drum member 172 in the first direction causes retraction of output cam bar 146 within the housing halves 106, 108. Conversely, retraction of input cam bar 112 in a proximal direction causes rotation of drum member 172 in a second direction and rotation of drum member 172 in the second direction causes advancement of output cam bar 146.

As noted above, tabs 152 are formed on the distal end 112b of input cam bar 112. As shown in FIGS. 17-19, tabs 152 are received through dwell slots 143 formed in proximal end 142a of pusher driver 142, through dwell slots 145 (FIG. 7) formed in proximal end 144a of knife driver 144, and through dwell slots 147 formed in output cam bar 146. As will be described in further detail below, dwell slots 143 formed in pusher driver 142 and dwell slots 145 formed in knife drivers 144 are dimensioned such that advancement of input cam bar 112 beyond a first distance "d1" (FIG. 50) advances pusher driver 142 and knife driver 144 during actuation of tool assembly 102. As will also be described in further detail below, dwell slots 147 formed in output cam bar 146 are configured such that output cam bar 146 is permitted to retract relative to input cam bar 112 during actuation of tool assembly 102 to cause retraction of anvil member 162 relative to cartridge cover 128 (FIG. 15). A latch 176 is formed on a proximal end of input cam bar 112 and is configured to be selectively engaged by safety lock assembly 118 (FIG. 5).

With particular reference to FIGS. 17 and 18, as noted above, drive member 116 is securely affixed to proximal end 112a of input cam bar 112 and connects input cam bar 112 to a drive shaft (not shown) extending through elongated body portion 18 (FIG. 1) of actuation unit 14 (FIG. 1) of surgical stapler 10 (FIG. 1). For a detailed description of the structure and function of an exemplary drive shaft and the connection of drive member 116 to an elongated body portion of an actuation unit, please refer to commonly owned U.S. Pat. No. 8,469,254 ("the '254 patent"), the disclosure of which is incorporated herein by reference in its entirety.

Figure 22:
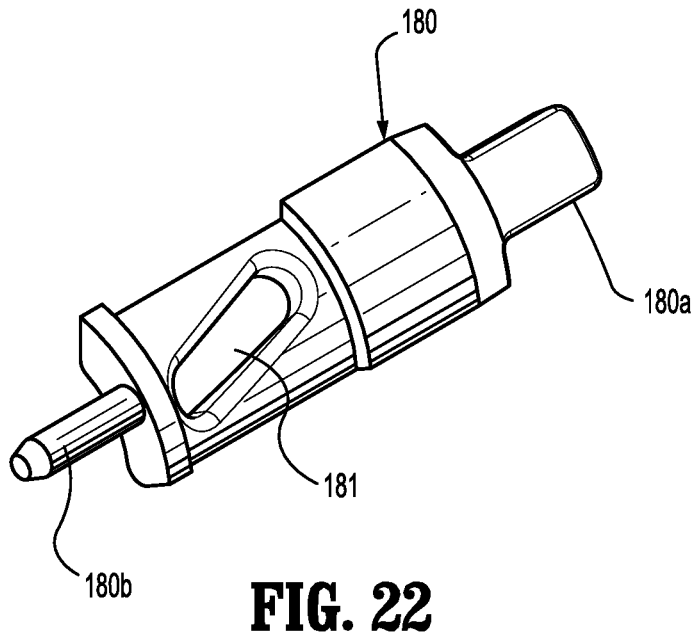
FIG. 22 is a perspective view of a linear actuator of the safety lock assembly shown in FIG. 20.
Figure 23:
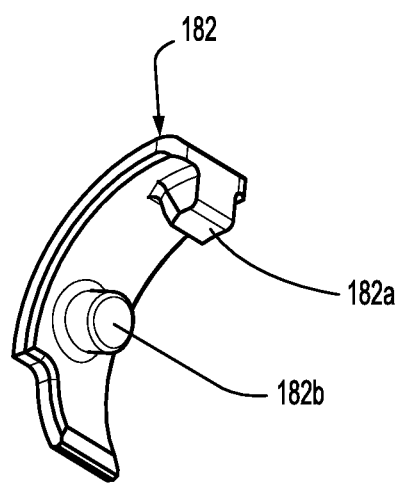
FIG. 23 is a perspective view of a lock member of the safety lock assembly shown in FIG. 20.

Safety lock assembly 118 of loading unit 12 will now be described with reference to FIGS. 20-27. Safety lock assembly 118 includes a linear actuator 180, a lock member 182, and a spring 184. Linear actuator 180 is slidably positioned within a longitudinal slot 179 formed in first housing half 106 of body portion 100 of loading unit 12 and is configured to move in a longitudinal direction. Linear actuator 180 includes an abutment member 180a on a proximal end and a spring guide 180b on a distal end. Linear actuator 180 defines a central cam slot 181 (FIG. 22). Spring 184 is disposed within first housing half 106 and engages spring guide 180b of linear actuator 180. Spring 184 biases linear actuator 180 in a proximal direction. Locking member 182 is slidably positioned within a transverse slot 183b of first housing half 106 of body portion 100 and is configured to move in a transverse direction during longitudinal advancement of linear actuator 180. Locking member 182 includes a radially inwardly extending cam member 182b (FIG. 23) and a radially inwardly extending finger 182a (FIG. 23). Cam member 182b is received within central cam slot 181 of linear actuator 180. In a first or locked position (FIGS. 24 and 25), finger 182a of locking member 182 engages latch 176 formed on proximal end 112a of input cam bar 112 to prevent input cam bar 112 from moving longitudinally within body portion 100, thereby preventing actuation of loading unit 12.

Figure 24:
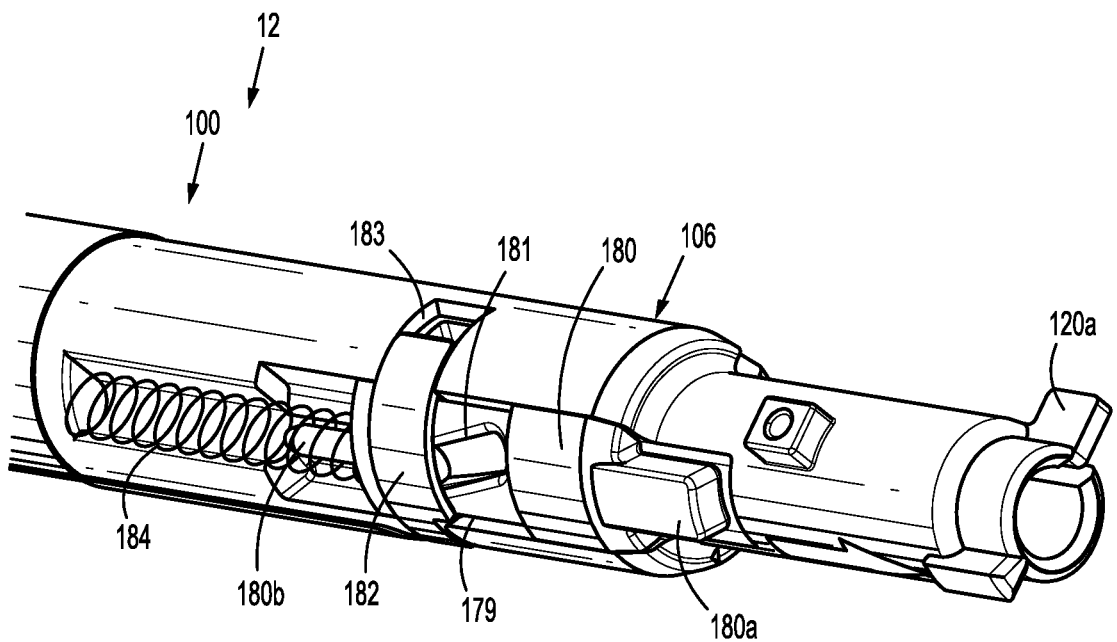
FIG. 24 is a perspective view of the proximal end of the loading unit shown in FIG. 20 with the safety mechanism in a first or locked position.
Figure 25:
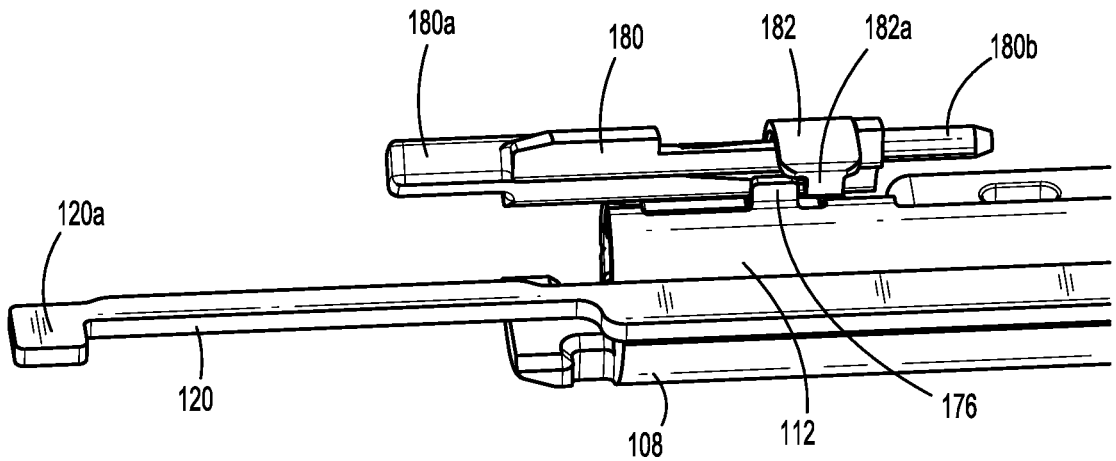
FIG. 25 is a side view of the proximal end of the loading unit shown in FIG. 20 with a first housing half removed.

With particular reference to FIGS. 24 and 25, safety lock assembly 118 is shown prior to attachment of loading unit 12 to elongated body portion 18 (FIG. 1) of actuation unit 14 (FIG. 1) of surgical stapler 10 (FIG. 1). Spring 184 urges linear actuator 180 to the proximal position. In the proximal position, linear actuator 180 cams finger 182a such that locking member 182 is moved to the locked position. As discussed above, in the locked position, finger 182a of locking member 182 engages latch 176 of input cam bar 112.

Figure 26:
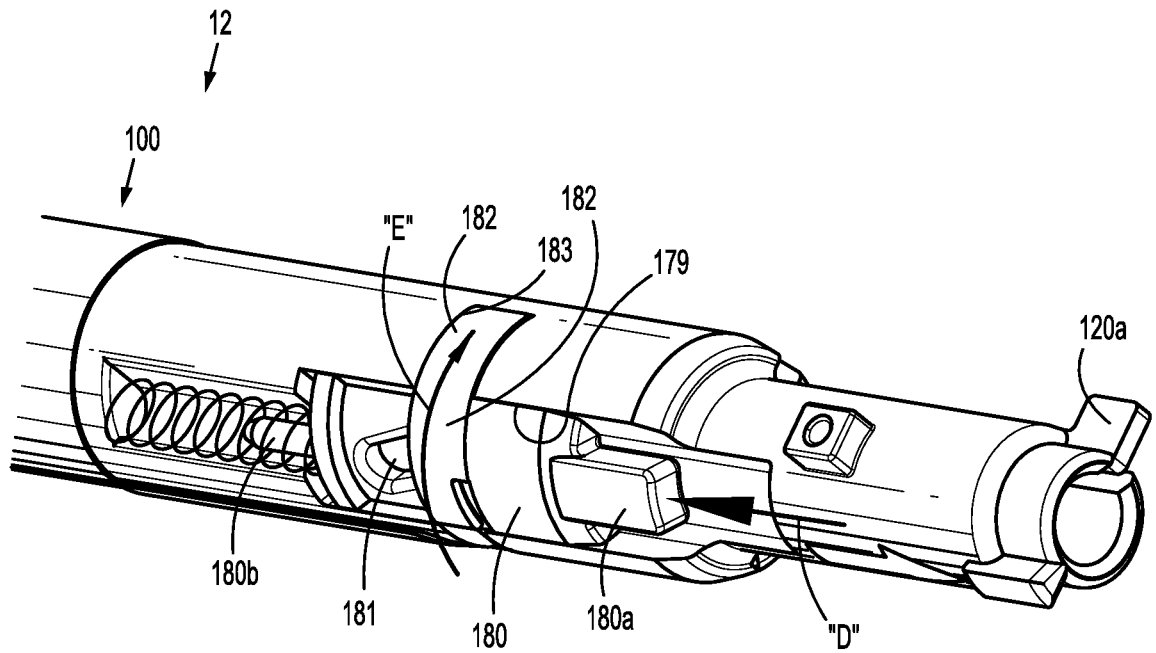
FIG. 26 is a perspective view of the proximal end of the loading unit shown in FIG. 20 with the safety lock assembly in a second or unlocked position.
Figure 27:
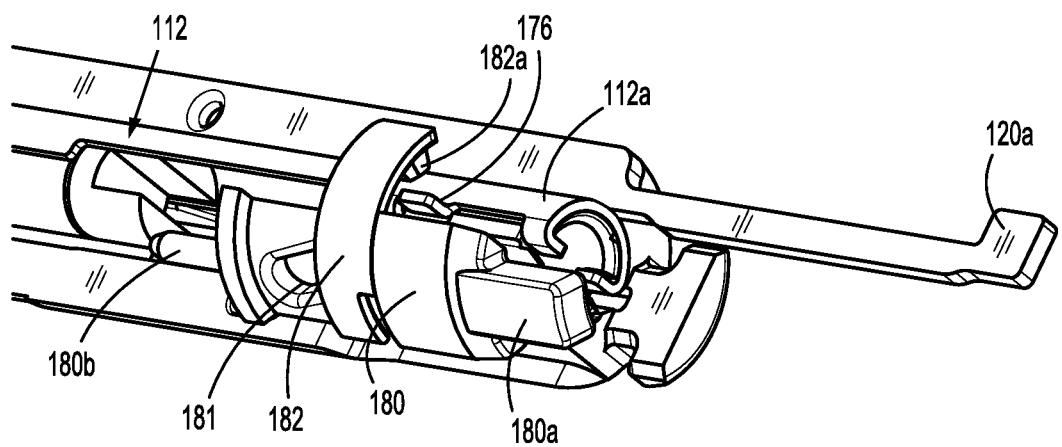
FIG. 27 is a perspective end view of the proximal end of the loading unit shown in FIG. 20 with a first housing half removed.

Turning to FIGS. 26 and 27, attachment of loading unit 12 to elongated body portion 18 (FIG. 1) of actuation unit 14 (FIG. 1) of surgical stapler 10 (FIG. 1) causes advancement of linear actuator 180, as indicated by arrow "D" shown in FIG. 26, against the bias of spring 184. As linear actuator 180 is advanced, cam member 182b of lock member 182 rides within central cam slot 181 of linear actuator 180. The angled configuration of central cam slot 181 causes locking member 182 to rotate relative to first housing half 106. Rotation of locking member 182 causes finger 182a of lock member 182 to disengage from latch 176 of input cam bar 112. Once finger 182a is disengaged from latch 176, input cam bar 112 may be moved longitudinally upon actuation of actuation unit 14 (FIG. 1). The safety lock assembly 118 prevents advancement of the input cam bar 112 until the loading unit 112 has been secured to an actuation unit 14. For a more detailed description of the structure and function of an exemplary safety lock assembly, please refer to the '254 patent, the content of which was previously incorporated herein by reference.

Tool assembly 102 of loading unit 12 will now be described in detail with reference to FIGS. 28-43. Referring initially to FIGS. 28-31, as noted above, tool assembly 102 is pivotally secured to body portion 100 of loading unit 100 by pivot pin 119 and includes outer sleeve 122, housing member 124, staple cartridge 126, and cartridge cover 128. Staple cartridge 126 is secured to housing member 124 through receipt of flanges 190 (FIG. 6B) of housing member 124 within notches 191 (FIG. 6B) of staple cartridge 126. Although staple cartridge 126 is shown secured to housing member 124 through receipt of flanges 190 within notches 191, staple cartridge 126 may be secured to housing member 124 in any suitable manner. Outer sleeve 122 of tool assembly 102 is positioned about housing member 124 and staple cartridge 126 to maintain the staple cartridge 126 securely attached to the housing member 124. Cartridge cover 128 secures outer cover 122 about housing member 124 and staple cartridge 126 through a snap-fit arrangement, or in any other suitable manner.

With particular reference now to FIGS. 31-33, housing member 124 and staple cartridge 126 operably receive a distal end of pusher assembly 220 (FIG. 7). In particular, flexible portion 142c of pusher driver 142 is slidably received within first longitudinal channel 201 in housing member 124. Pusher driver 142 is maintained within first longitudinal channel 201 by first securement pin 150 and bearing rings 150a, 150b. Specifically, bearing rings 150a, 150b which rotate about securement pin 150 engage pusher driver 142 to facilitate longitudinal movement of pusher driver 142 relative to housing member 124.

Figure 57:
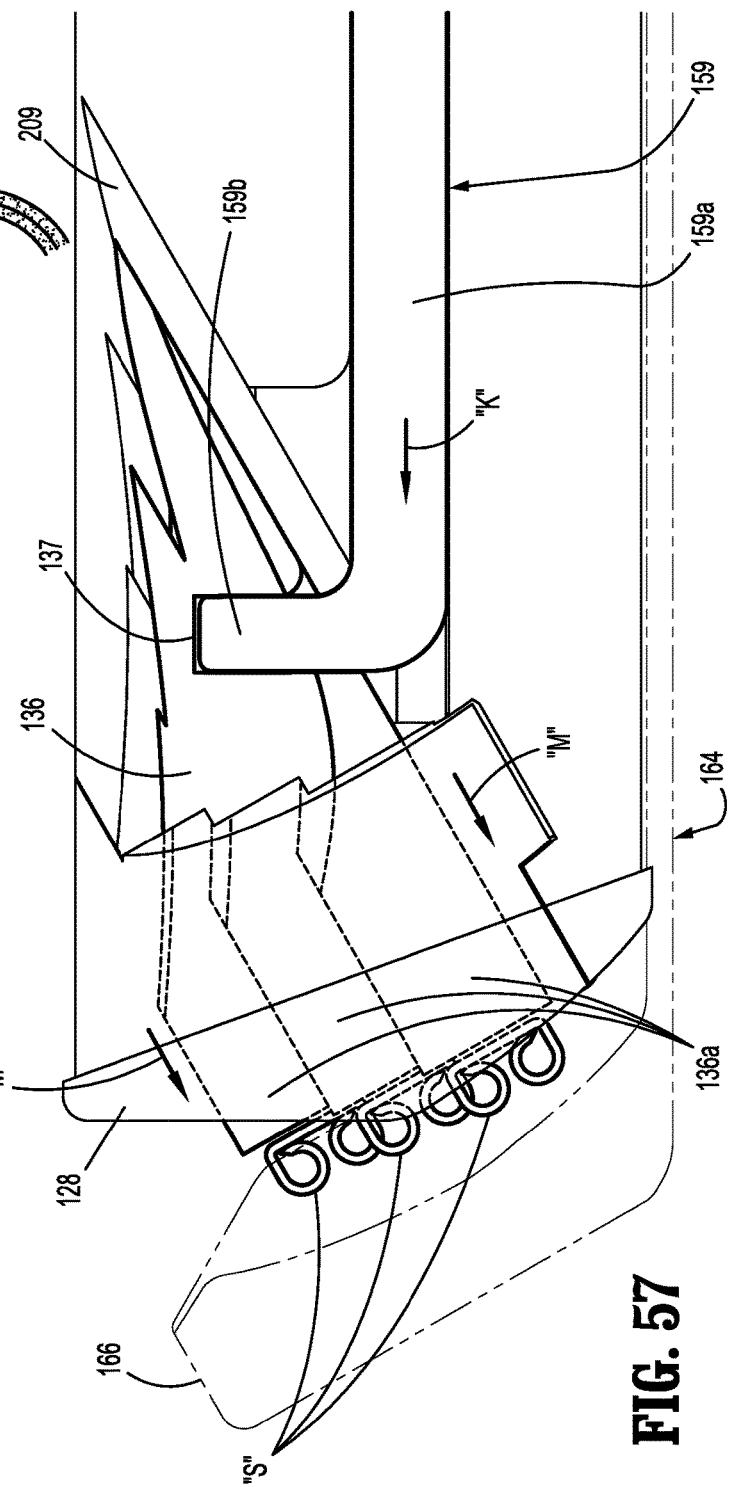
FIG. 57 is an enlarged side view of the distal end of the tool assembly shown in FIG. 55 with the anvil assembly shown in phantom.

Semi-annular flange 158 of pusher driver 142 is slidably received within semi-annular cutout 203 in housing member 124 and is movable between a retracted position (FIG. 54) and an advanced position (FIG. 57). Elongated portions 159a of engagement members 159 of pusher driver 142 are slidably received within longitudinal cutouts 205 of housing member 124. Elongated portions 159a of engagement members 159 extend from longitudinal cutouts 205 of housing member 124 and are slidably received within longitudinal cutouts 207 of staple cartridge 126. Engagement members 159 engage pusher members 136 of pusher driver 142 which are received within cutouts 209 in staple cartridge 126. Specifically, engagement portions 159b of engagement members 159 of pusher driver 142 are slidably received within grooves 137 of pusher members 136. The staple engagement portions 136a of pusher members 136 are slidably received within the plurality of notches 209a (FIG. 33) in staple cartridge 126 and are positioned to selectively a distal-most staple of each row of staples "S".

Figure 34:
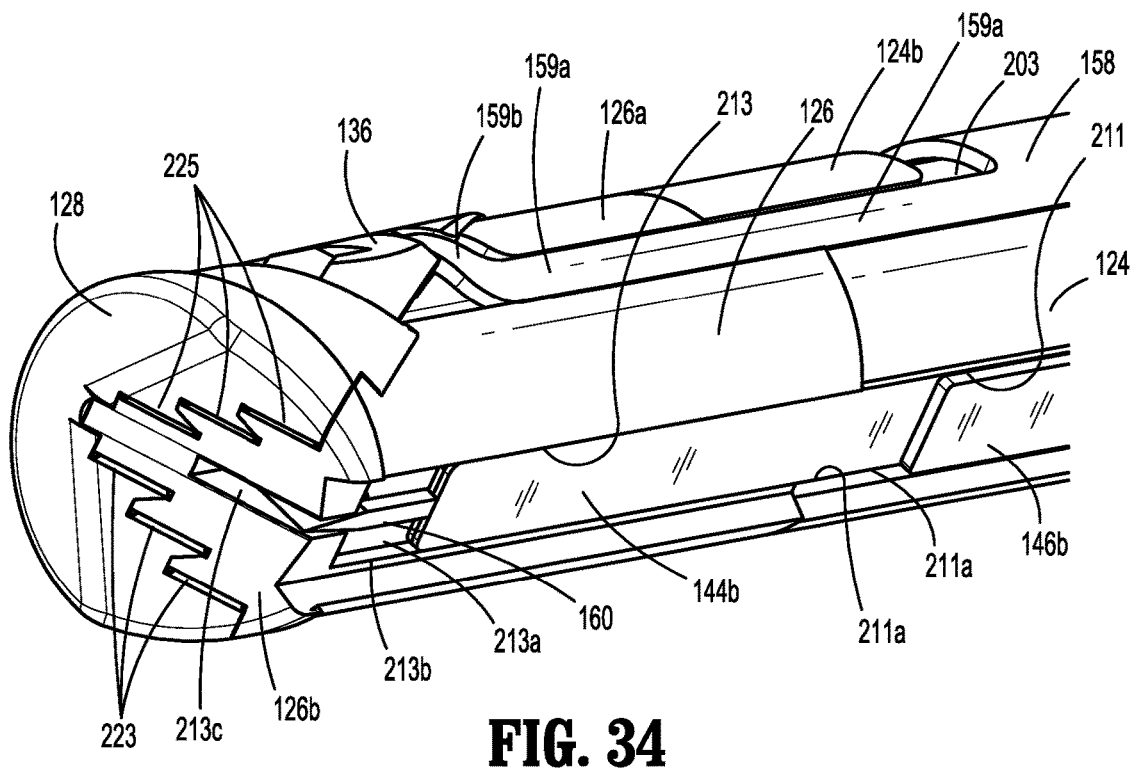
FIG. 34 is an enlarged perspective end view of the distal end of the tool assembly shown in FIG. 32 with outer sleeve of the tool assembly and the anvil member removed.
Figure 35:
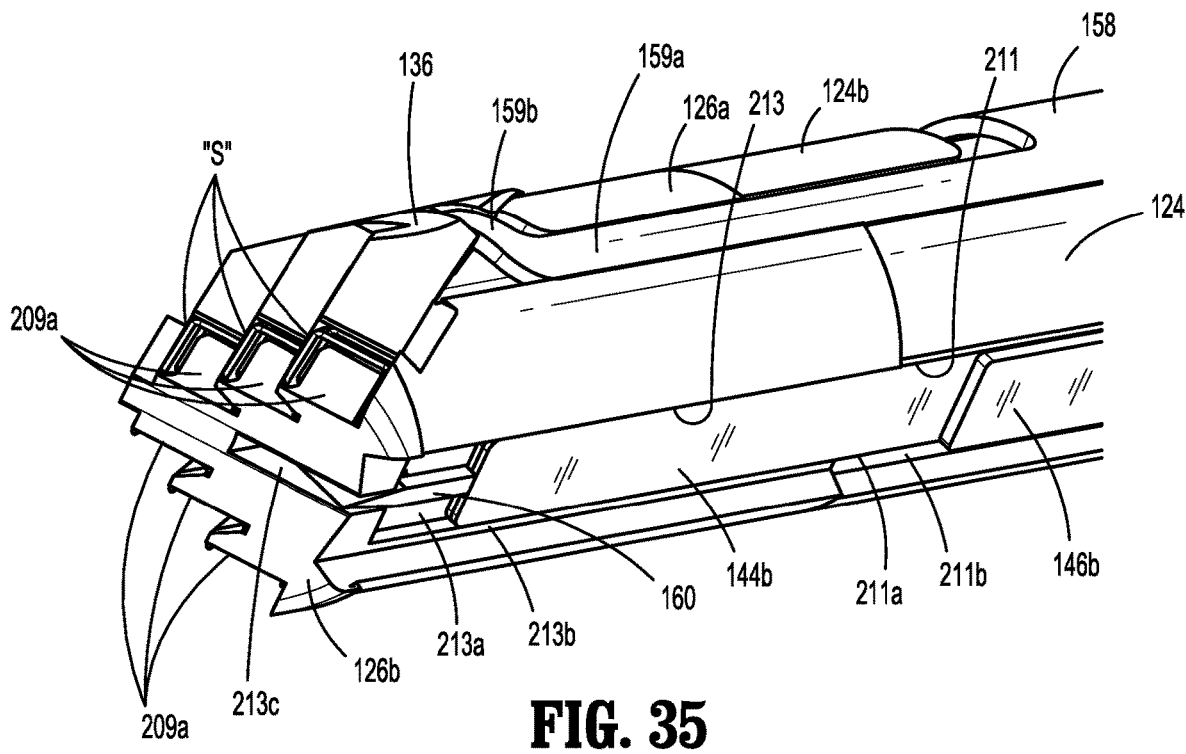
FIG. 35 is an enlarged perspective end view of the distal end of the tool assembly shown in FIG. 33 with the cartridge cover removed.
Figure 36:
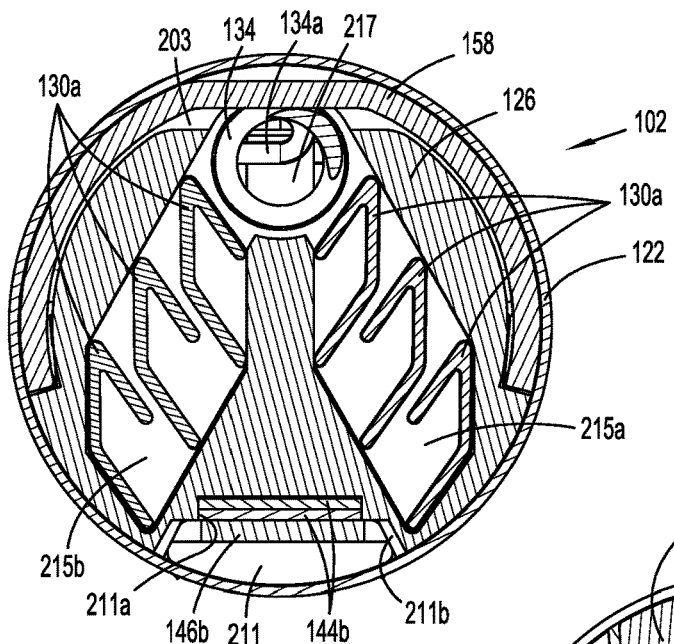
FIG. 36 is a cross-sectional view of the loading unit shown in FIG. 1 taken along section line 36-36 shown in FIG. 3.
Figure 37:
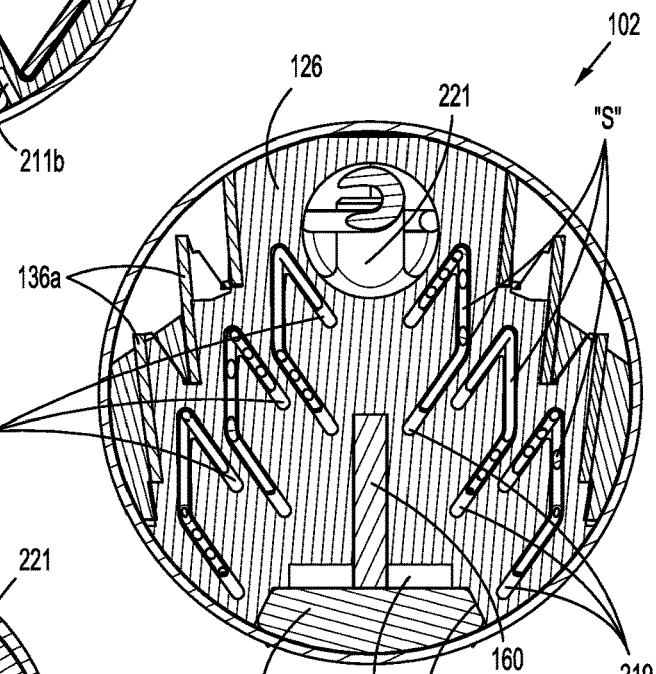
FIG. 37 is a cross-sectional view of the loading unit shown in FIG. 1 taken along section line 37-37 shown in FIG. 3.
Figure 38:
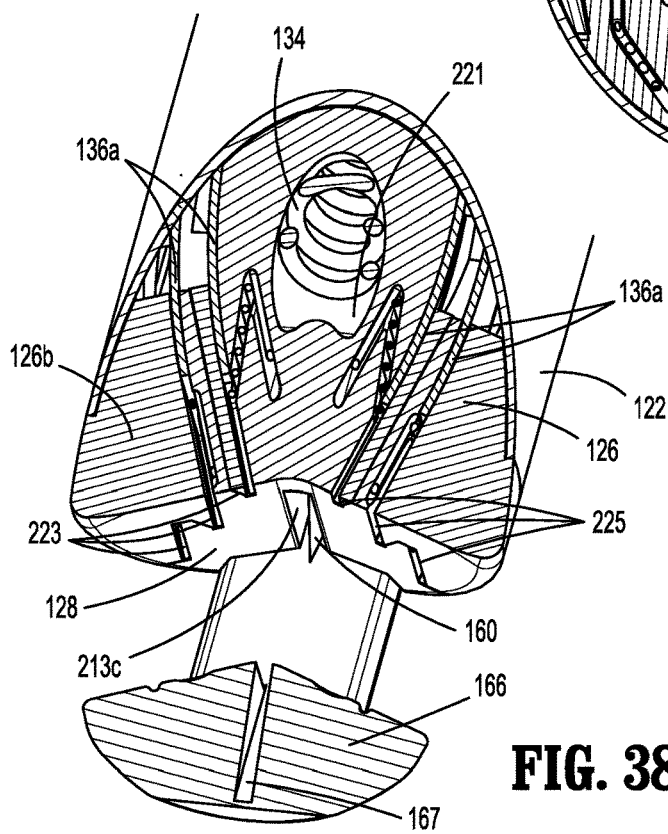
FIG. 38 is a cross-sectional view of the loading unit shown in FIG. 1 taken along section line 38-38 shown in FIG. 3.
Figure 39:
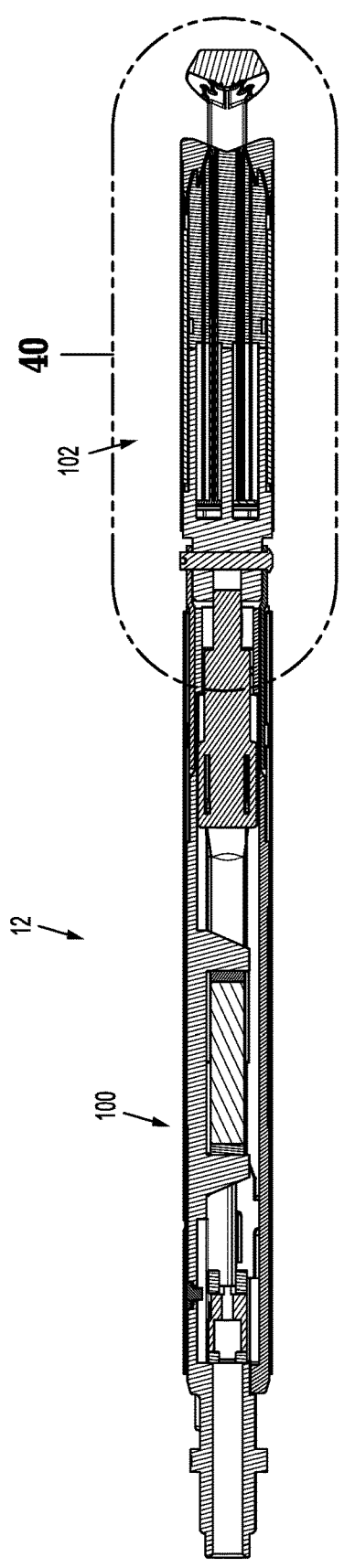
FIG. 39 is a cross-sectional view of the loading unit shown in FIG. 1 taken along section line 39-39 shown in FIG. 10.
Figure 40:
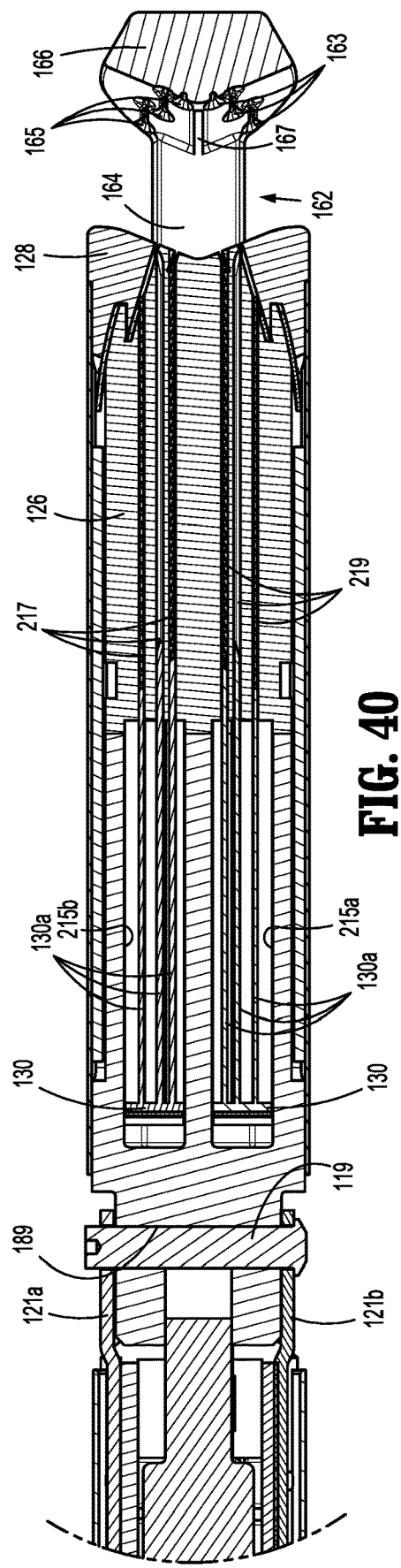
FIG. 40 is an enlarged view of the indicated area of detail shown in FIG. 39.
Figure 47:
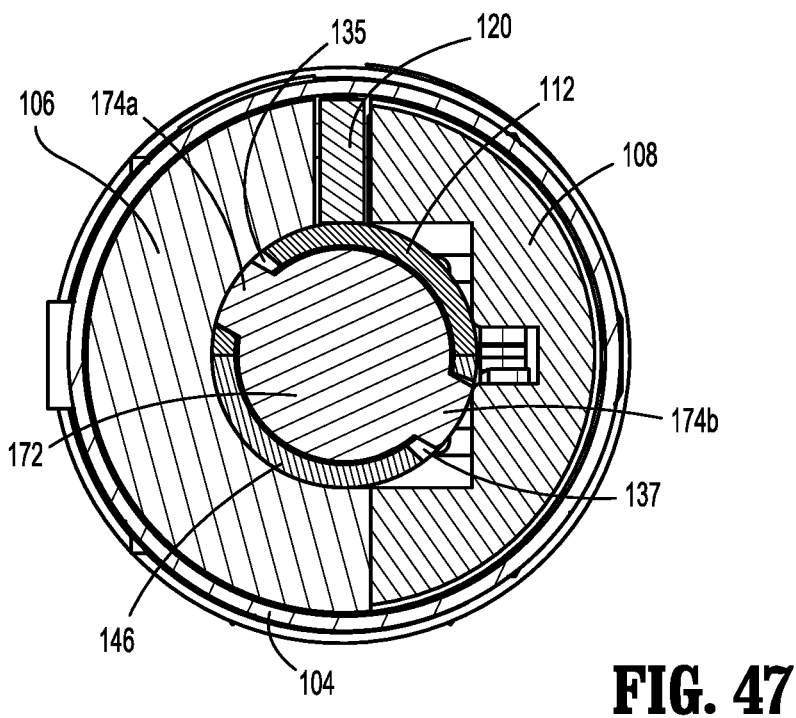
FIG. 47 is a cross-sectional end view of the functional components shown in FIG. 45 taken along section line 47-47 shown in FIG. 46.
Figure 48:
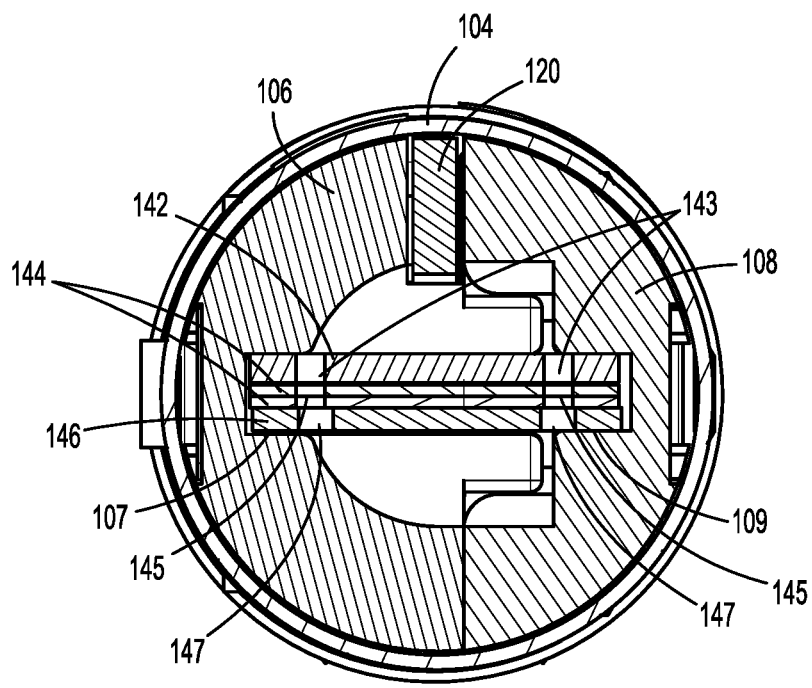
FIG. 48 is a cross-sectional end view of the functional components shown in FIG. 45 taken along section line 48-48 shown in FIG. 45.

Referring also to FIG. 34, housing member 124 and staple cartridge 126 further receive distal ends of knife driver assembly 230 (FIG. 8) and anvil assembly 240 (FIG. 9). In particular, the distal end 144b of knife driver 144 is slidably received within the inner portion 211a of second longitudinal channel 211 of housing member 124 and the distal end 146b of output cam bar 146 is slidably received within the outer portion 211b of second longitudinal channel 211 of housing member 124. Knife driver 144 and output cam bar 146 are maintained within second longitudinal channel 201 by second securement pin 154 and bearing ring 154a. Specifically, bearing ring 154a which rotates about second securement pin 154 engages output cam bar 146 to facilitate longitudinal movement of knife driver 144 and output cam bar 146 relative to housing member 124.

The distal end 144b of knife driver 144 is received within inner portion 213a of longitudinal channel 213 of staple cartridge 126 and the distal end 146b of output cam bar 146 and anvil 162 of anvil assembly 240 are received within outer portion 213b of longitudinal channel 213. The knife 160 which is mounted on the distal end 144b of knife driver 144 is received within longitudinally extending slot 213c of staple cartridge 126.

With particular reference now to FIGS. 36-44, housing member 124 and staple cartridge 126 are also configured to operably receive staple supply assembly 210. In particular, pressure plates 130 of staple supply assembly 210 is slidably received within each of first and second internal channels 215a, 215b. Spring clip 132 (FIG. 42) is secured to a proximal end of each pressure plate 130. A proximal end 134a of spring 134 is received through central bore 221 of housing member 124 and is secured to spring clip 132. Spring 134 acts on spring clip 132 to bias pressure plates 130 in a distal direction through first and second internal channels 215a, 215b. A row of staple "S" is received through each slot of first and second set of slots 217, 219 of staple cartridge 126. A distal end 134b of spring 134 extends through circular bore 221a of staple cartridge 126 and is secured to a retaining pin 222 (FIG. 33) which is positioned adjacent distal end 126b of staple cartridge 126. Extensions 130a of pressure plates 130 engage a proximal staple of each row of staples "S" to urge the row of staples "S" distally towards engagement portions 136a of pusher members 136.

Cartridge cover 128 and distal end 126b of staple cartridge 126 define first and second sets of openings 223, 225 (FIG. 38) which are positioned adjacent distal ends of respective slots 217, 219 (FIG. 37) in staple cartridge 126. The staples "S" are ejected by pusher members 136 through the openings 223, 225. First and second set of openings 223, 225 are aligned with respective staple forming pockets 163, 165 formed in anvil 166 of anvil member 162.

The operation of loading unit 12 will now be described with reference to FIGS. 45-59. Referring initially to FIGS. 45-48, loading unit 12 is shown in an initial or unclamped position. In the unclamped position, first drum post 174a formed on drum member 172 of drum assembly 114 (FIG. 5) is disposed within a proximal end of helical portion 173b of slot 173 formed in input cam bar 112 and second drum post 174b formed on drum member 172 is disposed in a proximal end of slot 175 formed in output cam bar 146. In the unclamped position, anvil 166 of anvil bar 146 is longitudinally spaced from cartridge cover 128 (FIG. 49) of tool assembly 102.

FIGS. 49-54 illustrate loading unit 12 in a clamped position. Movement of loading unit 12 from the unclamped position to the clamped position is caused by advancing input cam bar 112 of loading unit 12 in a distal direction. More specifically, as input cam bar 112 is advanced distally in response to operation of actuation unit 14, a first distance "d1", as indicated by arrow "E" in FIG. 50, first drum post 174a formed on drum member 172 traverses helical portion 173b of slot 173 in input cam bar 112 causing drum member 172 to rotate in a first direction, as indicated by arrow "F" in FIG. 51. Rotation of drum member 172 in the first direction relative to output cam bar 146 moves second drum post 174b formed on drum member 172 within slot 175 formed in output cam bar 146. Movement of second drum post 174b relative to output cam bar 146 causes output cam bar 146 to retract, as indicated by arrow "G" in FIG. 50. Retraction of output cam bar 146 moves anvil member 162 relative to cartridge cover 128, as indicated by arrow "H" in FIG. 49.

As noted above, dwell slots 174 formed in output cam bar 146 are dimensioned to permit movement of output cam bar 146 relative to input cam bar 112. Dwell slots 143 (FIG. 53) formed in pusher driver 142 and dwell slots 145 (FIG. 8) formed in knife driver 144 are also dimensioned to permit advancement of input cam bar 112 relative to pusher driver 142 and knife driver 144. In particular, the length of dwell slots 143, 145 of respective pusher driver 142 and knife driver 144 is such that tabs 152 formed on distal end 112b of input cam bar 112 traverse therethrough as input cam bar 112 is advanced the first distance "d1".

The length of dwell slots 143, 145 of respective pusher driver 142 and knife drive 144 is such that advancement of input cam bar 112 beyond the first distance "d1," as indicated by arrow "J" in FIG. 55, causes tabs 152 to engage each of pusher driver 142 and knife driver 144. Once tabs 152 of input cam bar 112 engage pusher driver 142 and knife driver 144, continued advancement of input cam bar 112 causes advancement of pusher driver 142 in the distal direction, as indicated by arrow "K" in FIG. 56, and advancement of knife driver 144 in the distal direction, as indicated by arrow "L" in FIG. 56. It is envisioned that dwell slots 143, 145 of respective pusher driver 142 and knife driver 144 may be configured such that pusher driver 142 and knife driver 144 are advanced simultaneously or the advancement of knife driver 144 is delayed relative to the advancement of pusher driver 142 to allow for the stapling of tissue "T" prior to cutting of tissue "T". Receipt of first drum post 174*a* within longitudinal portion 173*a* of slot 173 formed in input cam bar 112 permits advancement of input cam bar 112 relative to drum member 172 without causing drum member 172 to rotate. In this manner, output cam bar 146 is maintained in the retracted position during continued advancement of input cam bar 146 relative to drum member 172.

Figure 56:
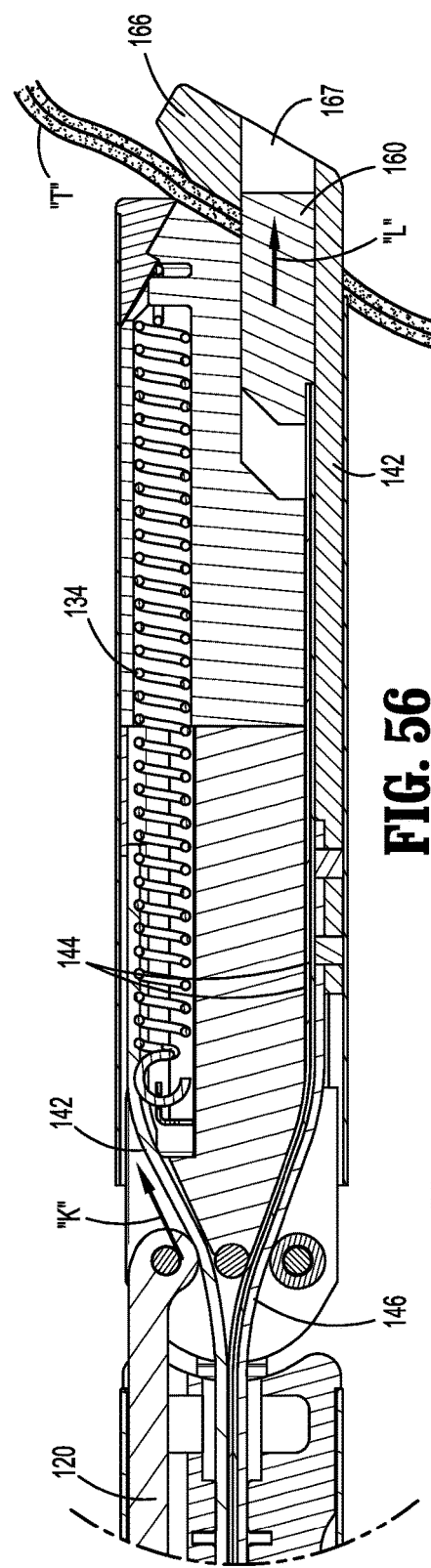
FIG. 56 is the view of the tool assembly shown in FIG. 11 in an actuated position.

With reference now to FIGS. 55-57, loading unit 12 is shown in a fully-actuated position. Loading unit 12 is moved to the fully-actuated position through advancement of input cam bar 112 in the distal direction a second distance "d2" (FIG. 55). As loading unit 12 is moved beyond the first distance "d1" and to the fully-actuated position, pusher driver 142 is advanced distally to staple tissue "T" (FIG. 56) and knife driver 144 is advanced distally to cut tissue "T". In particular, and with reference to FIGS. 56 and 57, as pusher driver 142 is advanced, engagement portion 159*b* of engagement members 159 of pusher driver 142 engage pusher members 136 causing pusher members 136 to advance relative to anvil 166 of anvil member 164, as indicated by arrows "M" in FIG. 57. As pusher members 136 are advanced, each engagement portions 136*a* of each pusher member 136 contacts a distal-most staple in a row of staples "S" and forces the distal-most staple out through openings 223, 225 formed between distal end 126*b* of staple cartridge 126 and cartridge cover 127, through tissue "T," and into engagement with staple forming pockets 163, 165 (FIG. 33) of anvil 166. As knife driver 144 is advanced, knife 160 is advanced through tissue "T" and into slot 167 formed between staple forming pockets 163, 165.

After loading unit 12 reaches the fully-actuated position, retraction of input cam bar 112 causes sequential retraction of pusher driver 142 and knife driver 144 and advancement anvil member 162 to an unclamped position. When the pusher driver 142 is retracted, the engagement portions 136*a* of pusher members 136 are retracted to a position to allow a subsequent staple "S" of each row of staples to be positioned into of notches 209*a* (FIG. 32) formed in distal end 126*b* of staple cartridge 126. As noted above, spring 134 of stapling supply assembly 210 biases pressure plates 130 distally to urge the rows of staples "S" distally into alignment with engagement portions 136*a* of pusher members 136. Once input cam bar 112 is returned to its initial position, loading unit 12 is ready for the subsequent actuation. It is envisioned that input cam bar need not return completely to the pre-actuated position before loading unit 12 can be subsequently actuated.

Figure 59:
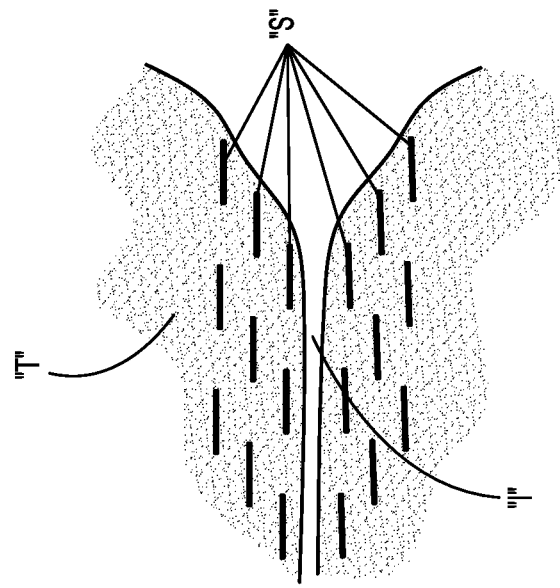
FIG. 59 is a top view of tissue stapled and cut using the surgical staple shown in FIG. 1.
Figure 58:
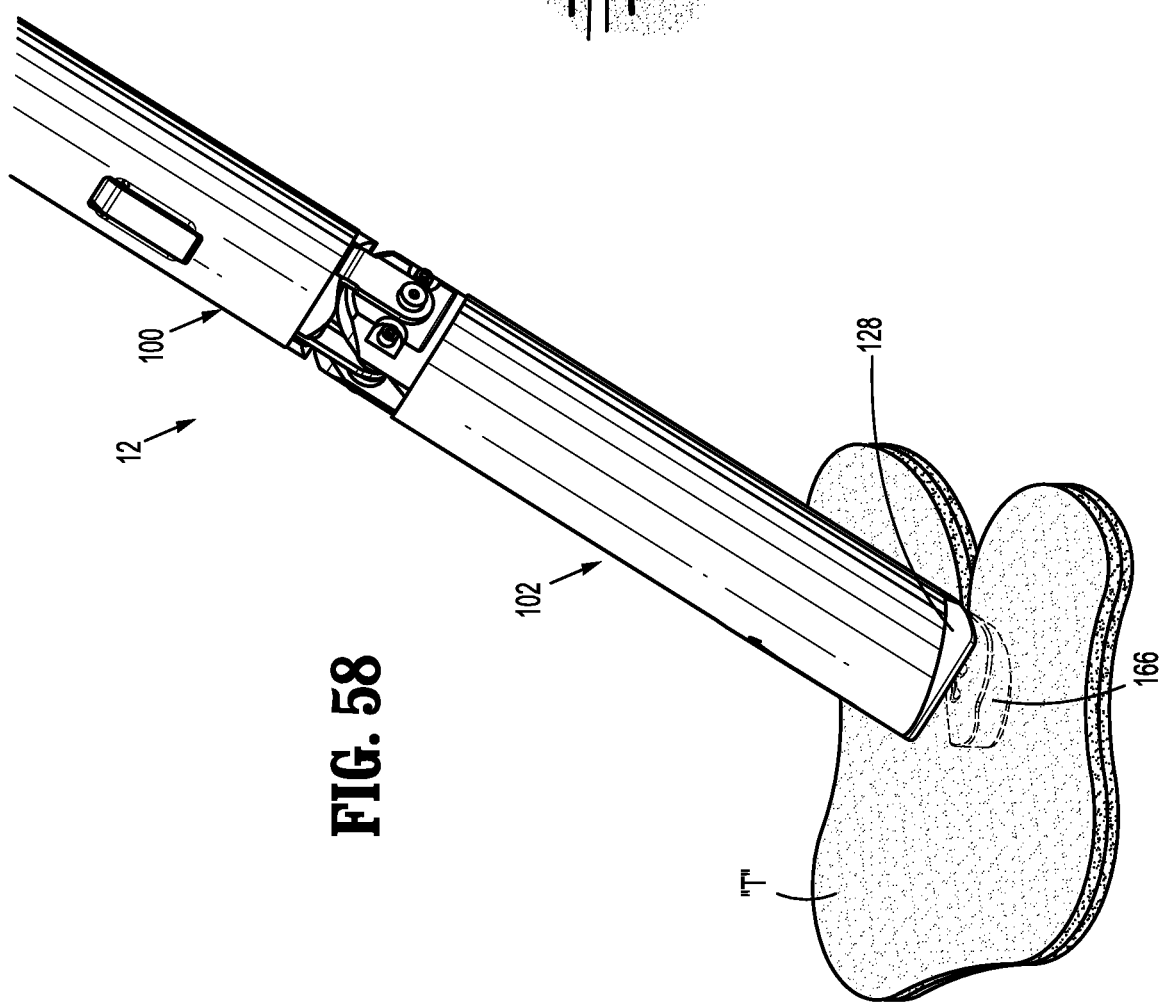
FIG. 58 is a perspective view of the tool assembly of the loading unit shown in FIG. 1 in use stapling and cutting tissue.

With reference now to FIGS. 58 and 59, in use, actuation unit 14 (FIG. 1) is manipulated such that loading unit 12 is disposed adjacent tissue "T" to be stapled and cut. As described above, tool assembly 102 of loading unit 12 may be articulated relative to body portion 100 of loading unit 12 to facilitate positioning of tissue "T" between anvil 166 and cartridge cover 128. Once tissue "T" is properly positioned, handle assembly 16 (FIG. 16) of actuation unit 12 may be actuated to cause the clamping of tissue "T". Continued actuation of handle assembly 16 causes stapling and cutting to tissue "T". After a complete actuation of handle assembly 16, loading unit 12 may be repositioned relative to tissue "T" and a second actuation of handle assembly 16 may be performed to clamp, staple, and cut tissue. This process may be repeated as necessary to complete a given procedure.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

The invention claimed is:

1. A surgical apparatus comprising:
an actuation assembly;
a body portion releasably coupled to the actuation assembly and defining a longitudinal axis;
a first member slidable within the body portion along the longitudinal axis, the first member including an input cam bar and a set of tabs on a distal portion of the input cam bar;
a second member rotatably supported within the body portion about the longitudinal axis and operably connected to the first member;
a third member slidable within the body portion along the longitudinal axis and extending distally from the body portion, the third member being operably connected to the second member, wherein linear movement of the first member causes rotational movement of the second member which causes linear movement of the third member; and
a fourth member slidable within the body portion, wherein linear movement of the first member causes linear movement of the fourth member.

2. The surgical apparatus of claim 1, wherein the fourth member extends distally from the body portion.

3. The surgical apparatus of claim 1, further including a fifth member slidable within the body portion, wherein linear movement of the first member causes linear movement of the fifth member.

4. The surgical apparatus of claim 3, wherein the fifth member extends distally from the body portion.

5. A surgical apparatus comprising:
a body portion defining a longitudinal axis;
a first member slidable within the body portion along the longitudinal axis;
a second member rotatably supported within the body portion about the longitudinal axis and operably connected to the first member, the second member including a drum member and first and second drum posts on the drum member;
a third member slidable within the body portion along the longitudinal axis and extending distally from the body portion, the third member being operably connected to the second member, wherein linear movement of the first member causes rotational movement of the second member which causes linear movement of the third member.

6. A surgical apparatus comprising:
an actuation assembly;
a body portion releasably coupled to the actuation assembly and defining a longitudinal axis;
a first member slidable within the body portion along the longitudinal axis;
a second member rotatably supported within the body portion about the longitudinal axis and operably connected to the first member;
a third member slidable within the body portion along the longitudinal axis and extending distally from the body portion, the third member being operably connected to the second member and including an output cam member, wherein linear movement of the first member a first distance in a distal direction causes rotational movement of the second member which causes linear movement of the third member in a proximal direction.

7. The surgical apparatus of claim 1, wherein the fourth member includes a pusher member and a semi-annular flange on a distal portion of the pusher member.

8. The surgical apparatus of claim 3, wherein the fifth member includes a knife driver.

9. The surgical apparatus of claim 1, wherein the linear movement of the first member a first distance in a distal direction causes the linear movement of the third member in a proximal direction.

10. The surgical apparatus of claim 1, wherein the linear movement of the first member a second distance in the distal direction causes linear movement of the fourth member in a proximal direction.

11. The surgical apparatus of claim 3, wherein the linear movement of the first member a third distance in the distal direction causes linear movement of the fifth member in a distal direction.

12. The surgical apparatus of claim 5, further including a fourth member slidable within the body portion, wherein linear movement of the first member causes linear movement of the fourth member.

13. The surgical apparatus of claim 12, further including a fifth member slidable within the body portion, wherein linear movement of the first member causes linear movement of the fifth member.

14. The surgical apparatus of claim 5, wherein the linear movement of the first member a first distance in a distal direction causes the linear movement of the third member in a proximal direction.

15. The surgical apparatus of claim 12, wherein the linear movement of the first member a second distance in the distal direction causes linear movement of the fourth member in a proximal direction.

16. The surgical apparatus of claim 6, further including a fourth member slidable within the body portion, wherein linear movement of the first member causes linear movement of the fourth member.

17. The surgical apparatus of claim 16, further including a fifth member slidable within the body portion, wherein linear movement of the first member causes linear movement of the fifth member.

18. The surgical apparatus of claim 16, wherein the linear movement of the first member a second distance in the distal direction causes linear movement of the fourth member in a proximal direction.

* * * * *